United States Patent
Faler et al.

(10) Patent No.: US 10,195,589 B2
(45) Date of Patent: Feb. 5, 2019

(54) BRIDGED BI-AROMATIC LIGANDS AND OLEFIN POLYMERIZATION CATALYSTS PREPARED THEREFROM

(71) Applicant: Univation Technologies, LLC, Houston, TX (US)

(72) Inventors: Catherine Anne Faler, Houston, TX (US); C. Jeff Harlan, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 15/567,713

(22) PCT Filed: Apr. 19, 2016

(86) PCT No.: PCT/US2016/028268
§ 371 (c)(1),
(2) Date: Oct. 19, 2017

(87) PCT Pub. No.: WO2016/172097
PCT Pub. Date: Oct. 27, 2016

(65) Prior Publication Data
US 2018/0147562 A1    May 31, 2018

Related U.S. Application Data

(60) Provisional application No. 62/150,124, filed on Apr. 20, 2015.

(51) Int. Cl.
| | | |
|---|---|---|
| B01J 23/44 | (2006.01) |
| C07C 43/225 | (2006.01) |
| C07F 7/00 | (2006.01) |
| B01J 31/38 | (2006.01) |
| C08F 10/00 | (2006.01) |
| C07C 43/205 | (2006.01) |
| C07C 43/23 | (2006.01) |
| B01J 31/22 | (2006.01) |

(52) U.S. Cl.
CPC ............. *B01J 23/44* (2013.01); *B01J 31/38* (2013.01); *C07C 43/2055* (2013.01); *C07C 43/225* (2013.01); *C07C 43/23* (2013.01); *C07F 7/003* (2013.01); *C08F 10/00* (2013.01); *B01J 31/2239* (2013.01); *B01J 2531/0258* (2013.01); *B01J 2531/48* (2013.01)

(58) Field of Classification Search
None
See application file for complete search history.

(56) References Cited

U.S. PATENT DOCUMENTS

2008/0269470 A1    10/2008    Boussie et al.

OTHER PUBLICATIONS

International Preliminary Report on Patentability for related PCT Application PCT/US2016/028268, dated Nov. 2, 2017 (7 pgs).
International Search Report & Written Opinion for related PCT Application PCT/US2016/028268, dated Jun. 24, 2016 (11 pgs).
Wu, et al., "Three-Dimensional Metal-Organic Frameworks Based on Functionalized Tetracarboxylate Linkers: Synthesis, Structures, and Gas Sorption Studies"; Inorganic Chemistry Article, vol. 48 (2009) (8 pgs).

*Primary Examiner* — Clinton A Brooks
(74) *Attorney, Agent, or Firm* — Brooks, Cameron & Huebsch, PLLC

(57) ABSTRACT

Disclosed are novel bridged bi-aromatic phenol ligands and transition metal catalyst compounds derived therefrom. Also disclosed are methods of making the ligands and transition metal compounds, and polymerization processes utilizing the transition metal compounds for the production of olefin polymers.

20 Claims, 5 Drawing Sheets

(7)

(8)

(9)

(10)

(11)

(12)

(13)

(14)

(15)

(16)

(17)

(18)

(19)

BRIDGED BI-AROMATIC LIGANDS AND OLEFIN POLYMERIZATION CATALYSTS PREPARED THEREFROM

This application is a National Stage Application under 35 U.S.C. § 371 of International Application Number PCT/US2016/028268, filed Apr. 19, 2016 and published as WO 2016/172097 on Oct. 27, 2016, which claims the benefit to U.S. Provisional Application 62/150,124, filed Apr. 20, 2015, the entire contents of which are incorporated herein by reference in its entirety.

FIELD

The present disclosure is directed to bridged bi-aromatic ligands and transition metal compounds prepared therefrom. The disclosure is also directed to methods of preparing the ligands and transition metal compounds, and to methods of using the transition metal compounds as catalyst components in olefin polymerization.

BACKGROUND

A major focus of the polyolefin industry in recent years has been on the development of new catalysts that deliver new and improved products. Bulky ligand transition metal compounds, for example, are now widely utilized in catalyst compositions to produce polyolefin polymers, such as polyethylene polymers.

It is recognized in the art that small differences in the molecular structure of a catalyst compound can greatly impact catalyst performance and that this is often governed by ligand structure. Therefore considerable effort has been expended in designing new ligand structures that may lead to catalysts of enhanced performance. WO 03/09162 discloses bridged bi-aromatic ligands, methods for their preparation and transition metal compounds derived therefrom.

It would be desirable to provide new bridged bi-aromatic ligands and methods for their synthesis. It would also be desirable to provide new transition metal compounds that can polymerize olefins with useful activity.

SUMMARY

In one aspect there is provided a bridged bi-aromatic phenol ligand of formula

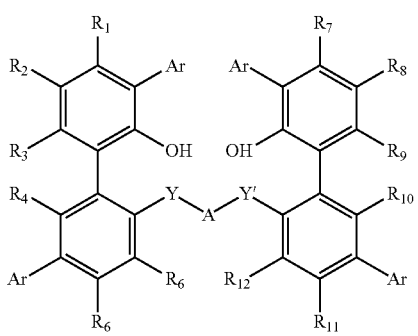

(I)

wherein each of $R^1$, $R^2$, $R^3$, $R^4$, $R^5$, $R^6$, $R^7$, $R^8$, $R^9$, $R^{10}$, $R^{11}$ and $R^{12}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is a bridging group having from one to 50 non-hydrogen atoms; Y and Y' are independently selected from O, S, $NR^a$ and $PR^a$ wherein $R^a$ is optionally substituted hydrocarbyl; Ar is, independently, optionally substituted aryl or optionally substituted heteroaryl.

Each of $R^1$, $R^2$, $R^3$, $R^4$, $R^5$, $R^6$, $R^7$, $R^8$, $R^9$, $R^{10}$, $R^{11}$ and $R^{12}$ may be independently selected from the group consisting of hydride, halide, and optionally substituted alkyl, heteroalkyl, aryl, heteroaryl, alkoxyl, aryloxyl, silyl, boryl, dialkylamino, alkylthio, arylthio and seleno.

Each of $R^1$, $R^2$, $R^3$, $R^4$, $R^5$, $R^6$, $R^7$, $R^8$, $R^9$, $R^{10}$, $R^{11}$ and $R^{12}$ may be independently selected from the group consisting of hydride, halide, and optionally substituted alkyl, heteroalkyl, aryl, heteroaryl, alkoxyl and aryloxyl.

Each of $R^1$, $R^2$, $R^3$, $R^4$, $R^5$, $R^6$, $R^7$, $R^8$, $R^9$, $R^{10}$, $R^{11}$ and $R^{12}$ may be independently selected from the group consisting of hydride, fluoro, chloro, and optionally substituted alkyl, heteroalkyl, aryl and heteroaryl.

In any one of the hereinbefore embodiments the bridging group A may be selected from the group consisting of optionally substituted divalent hydrocarbyl and divalent heteroatom containing hydrocarbyl.

In any one of the hereinbefore disclosed embodiments the bridging group A may be selected from the group consisting of optionally substituted divalent alkyl, alkenyl, alkynyl, heteroalkyl, heteroalkenyl, heteroalkynyl, aryl, heteroaryl and silyl.

In any one of the hereinbefore disclosed embodiments the bridging group A may be represented by the general formula —$(QR^{13}_{2-z''})_{z'}$— wherein each Q is either carbon or silicon and each $R^{13}$ may be the same or different from the others such that each $R^{13}$ is selected from the group consisting of hydride and optionally substituted hydrocarbyl and heteroatom containing hydrocarbyl, and optionally two or more $R^{13}$ groups may be joined into a ring structure having from 3 to 50 atoms in the ring structure not counting hydrogen atoms; z' is an integer from 1 to 10; and z'' is 0, 1 or 2.

In any one of the hereinbefore disclosed embodiments Ar may be, independently, an optionally substituted phenyl, naphthyl, biphenyl, anthracenyl or phenanthrenyl.

In any one of the hereinbefore disclosed embodiments Ar may be, independently, an optionally substituted thiophene, pyridine, isoxazole, pyrazole, pyrrole, furan, or benzo-fused analogues of these rings.

In any one of the hereinbefore disclosed embodiments each occurrence of Ar is the same.

The bridged bi-aromatic phenol ligand of formula (I) may be of formula (II):

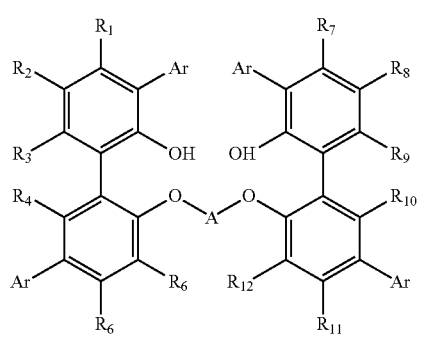

(II)

wherein each of $R^1$, $R^2$, $R^3$, $R^4$, $R^5$, $R^6$, $R^7$, $R^8$, $R^9$, $R^{10}$, $R^{11}$, $R^{12}$, Ar and A is as defined in any one of the hereinbefore disclosed embodiments.

In another aspect there is provided a method for preparing a bridged bi-aromatic phenol ligand of formula (I) or formula (II) the method comprising at least one step of halogenation of an aromatic ring and at least one step of aryl coupling.

The method may comprise at least one step of Negishi coupling. The method may comprise at least one step of Suzuki coupling. The method may comprise both at least one step of Negishi coupling and at least one step of Suzuki coupling.

The method may comprise the steps of:
a) treating a bridged bi-aromatic phenol of formula (III) with a source of halogen to yield a tetrahalo bridged bi-aromatic phenol of formula (IV); and

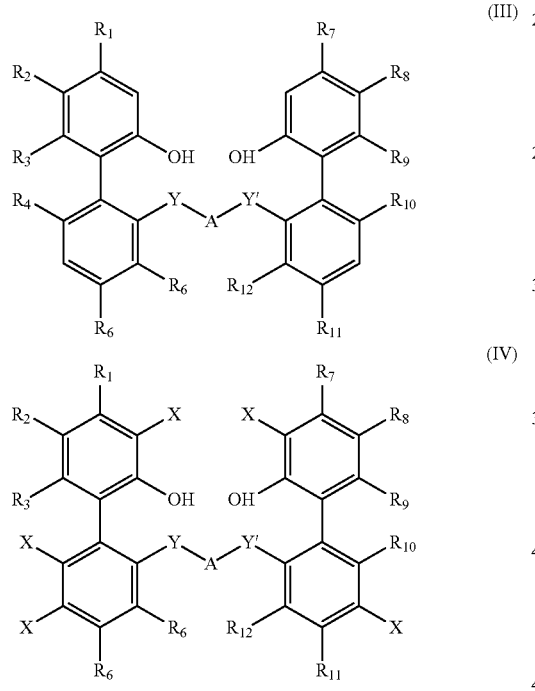

b) treating the tetrahalo bridged bi-aromatic phenol of formula (IV) with an aryl-boron compound (ArBR$^b_2$ or ArBF$_3^-$M$^+$) in the presence of a catalyst, to yield the bridged bi-aromatic phenol ligand of formula (I);
wherein each of $R^1$, $R^2$, $R^3$, $R^4$, $R^5$, $R^6$, $R^7$, $R^8$, $R^9$, $R^{10}$, $R^{11}$ and $R^{12}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more $R^1$ to $R^{12}$ groups can combine together into ring structures with such ring structures having from 3 to 100 non-hydrogen atoms in the ring; A is a bridging group having from one to 50 non-hydrogen atoms; Y and Y' are independently selected from O, S, NR$^a$ and PR$^a$ wherein R$^a$ is optionally substituted hydrocarbyl; Ar is, independently, optionally substituted aryl or optionally substituted heteroaryl; X is halo; R$^b$ is independently selected from hydride, alkyl, hydroxy and alkoxy, wherein when both of R$^b$ are alkoxy, optionally they may combine to form a ring structure of formula BO$_2$R$^b_2$, and wherein M$^+$ is an alkali metal cation.

The method may comprise the steps of:
a) treating a halophenol of formula (V) with a bridged diboron compound of formula (VI) in the presence of a catalyst to yield the bridged bi-aromatic phenol of formula (III);

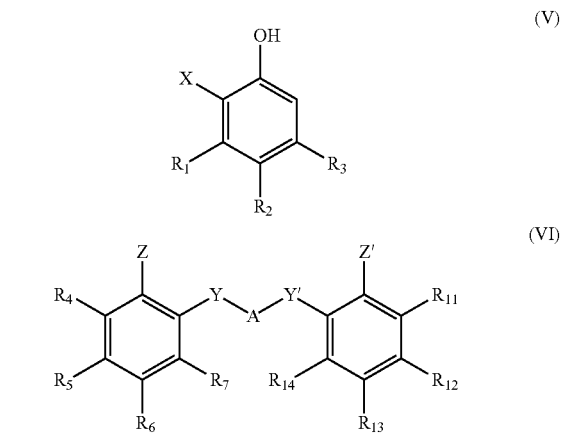

b) treating the bridged bi-aromatic phenol of formula (III) with a source of halogen to yield a tetrahalo bridged bi-aromatic phenol of formula (IV); and
c) treating the tetrahalo bridged bi-aromatic phenol of formula (IV) with an aryl-boron compound (ArBR$^b_2$ or ArBF$_3^-$M$^+$) in the presence of a catalyst, to yield the bridged bi-aromatic phenol ligand of formula (I);
wherein each of $R^1$, $R^2$, $R^3$, $R^4$, $R^5$, $R^6$, $R^7$, $R^8$, $R^9$, $R^{10}$, $R^{11}$ and $R^{12}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is a bridging group having from one to 50 non-hydrogen atoms; Y and Y' are independently selected from O, S, NR$^a$ and PR$^a$ wherein R$^a$ is optionally substituted hydrocarbyl; Z and Z' are independently selected from BR$^b_2$ and BF$_3^-$M$^+$, wherein R$^b$ is independently selected from hydride, alkyl, hydroxy and alkoxy, wherein when both of R$^b$ are alkoxy, optionally they may combine to form a ring structure of formula BO$_2$R$^b_2$, and wherein M$^+$ is an alkali metal cation; Ar is, independently, optionally substituted aryl or optionally substituted heteroaryl; X is halo.

In any one of the hereinbefore disclosed embodiments each of $R^1$, $R^2$, $R^3$, $R^4$, $R^5$, $R^6$, $R^7$, $R^8$, $R^9$, $R^{10}$, $R^{11}$ and $R^{12}$ may be independently selected from the group consisting of hydride, halide, and optionally substituted alkyl, heteroalkyl, aryl, heteroaryl, alkoxyl, aryloxyl, silyl, boryl, dialkylamino, alkylthio, arylthio and seleno.

In any one of the hereinbefore disclosed embodiments each of $R^1$, $R^2$, $R^3$, $R^4$, $R^5$, $R^6$, $R^7$, $R^8$, $R^9$, $R^{10}$, $R^{11}$, and $R^{12}$ may be independently selected from the group consisting of hydride, halide, and optionally substituted alkyl, heteroalkyl, aryl, heteroaryl, alkoxyl, aryloxyl, silyl, dialkylamino, alkylthio, and arylthio.

In any one of the hereinbefore disclosed embodiments the bridging group A may be selected from the group consisting of optionally substituted divalent hydrocarbyl and divalent heteroatom containing hydrocarbyl.

In any one of the hereinbefore disclosed embodiments the bridging group A may be selected from the group consisting of optionally substituted divalent alkyl, alkenyl, alkynyl, heteroalkyl, heteroalkenyl, heteroalkynyl, carbocycle, heterocarbocycle, aryl, heteroaryl and silyl.

In any one of the hereinbefore disclosed embodiments the bridging group A may be represented by the general formula —$(QR^{13}_{2-z''})_{z'}$— wherein each Q is either carbon or silicon and each $R^{13}$ may be the same or different from the others such that each $R^{13}$ is selected from the group consisting of hydride and optionally substituted hydrocarbyl and heteroatom containing hydrocarbyl, and optionally two or more $R^{13}$ groups may be joined into a ring structure having from 3 to 50 atoms in the ring structure not counting hydrogen atoms; z' is an integer from 1 to 10; and z'' is 0, 1 or 2.

A major advantage of the herein disclosed methods is that the number of reaction steps to access the ligands is low. For example, the disclosed ligands may be prepared from a bromophenol in three or four reaction steps.

In any one of the hereinbefore disclosed embodiments the catalyst may comprise a palladium or nickel catalyst.

In any one of the hereinbefore disclosed embodiments the palladium catalyst may comprise a palladium phosphine catalyst.

In any one of the hereinbefore disclosed embodiments the catalyst may further comprise a base.

In any one of the hereinbefore disclosed embodiments the base may comprise an alkali metal carbonate, alkali metal phosphate, alkali metal hydroxide, alkali metal alkoxide or an amine.

In any one of the hereinbefore disclosed embodiments X may be bromo or chloro. The source of halogen may be bromine or chlorine.

In any one of the hereinbefore disclosed embodiments the aryl-boron compound may be an optionally substituted arylborane or an optionally substituted heteroarylborane.

In any one of the hereinbefore disclosed embodiments the aryl-boron compound may be an optionally substituted aryl boronic acid or an optionally substituted heteroaryl boronic acid.

In any one of the hereinbefore disclosed embodiments the aryl-boron compound may be an optionally substituted aryl boronic ester or aryl cyclic boronic ester or an optionally substituted heteroaryl boronic ester or hetero aryl cyclic boronic ester.

In any one of the hereinbefore disclosed embodiments the aryl-boron compound may be an optionally substituted aryl trifluoroborate or an optionally substituted heteroaryl trifluoroborate.

In another aspect there is provided a ligand of formula (I) or formula (II) prepared by any one of the hereinbefore disclosed methods.

In another aspect there is provided a transition metal compound formed from any one of the hereinbefore disclosed ligands. The transition metal compound may comprise a titanium, a zirconium or a hafnium atom.

In another aspect there is provided a catalyst composition comprising one or more transition metal compounds as hereinbefore disclosed, and one or more activators. The activator may comprise one or more alumoxanes. The activator may comprise methylalumoxane.

In another aspect there is provided a supported catalyst composition comprising one or more transition metal compounds as hereinbefore disclosed, one or more activators and one or more support materials. The activator may comprise one or more alumoxanes. The activator may comprise methylalumoxane. The support may be silica.

The catalyst composition or supported catalyst composition may comprise two or more transition metal compounds. The transition metal compounds may be selected from any one of those hereinbefore disclosed or at least one of the transition metal compounds may be different from those hereinbefore disclosed. For example, at least one of the transition metal compounds may be a metallocene.

In another aspect there is provided a process for polymerizing olefins, the process comprising:
contacting olefins with one or more catalyst compositions or supported catalyst compositions comprising at least one transition metal compound as hereinbefore disclosed in a reactor under polymerization conditions to produce an olefin polymer or copolymer.

DETAILED DESCRIPTION

Figure 1:
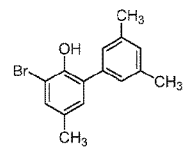
FIGS. 1 and 2 depict the chemical structures of exemplary compounds in accordance with the present disclosure.
Figure 1:
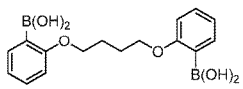
Figure 1:
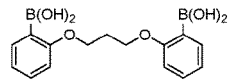
Figure 1:
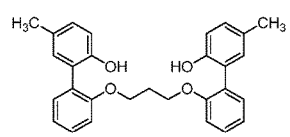
Figure 1:
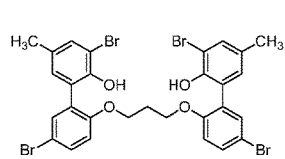
Figure 1:
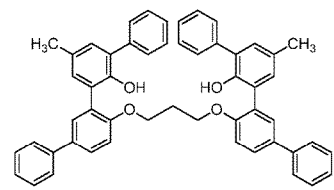
Figure 1:
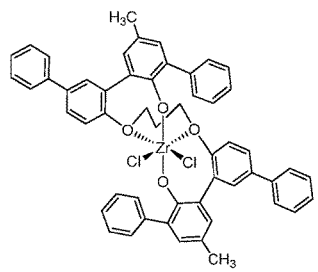
Figure 1:
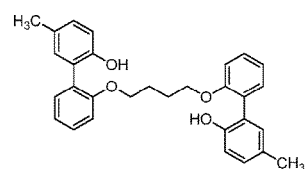
Figure 1:
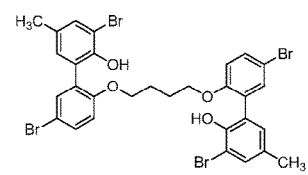
Figure 1:
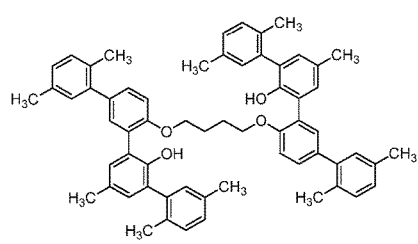
Figure 1:
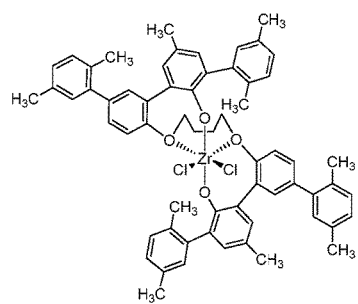
Figure 2:
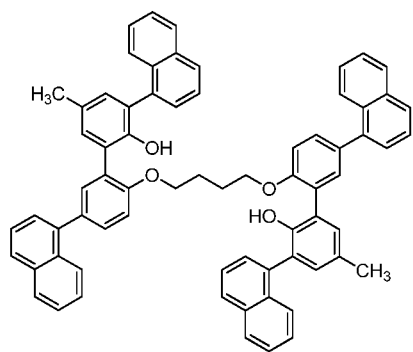
Figure 2:
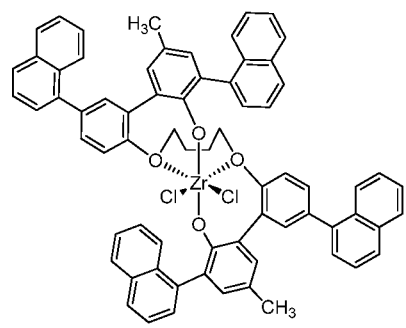

Before the present compounds, components, compositions, and/or methods are disclosed and described, it is to be understood that unless otherwise indicated this invention is not limited to specific compounds, components, compositions, reactants, reaction conditions, ligands, transition metal compounds, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified. Thus, for example, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

Disclosed herein are ligands, catalyst compounds, catalyst compositions and supported catalyst compositions for use in the polymerization of olefins which are advantageous to prepare and use. Also disclosed herein are methods of making the ligands, catalyst compounds, catalyst compositions and supported catalyst compositions and polymerization processes utilizing the catalyst compositions and supported catalyst compositions for the production of olefin polymers.

General Definitions

As used herein, a "catalyst composition" includes one or more catalyst compounds utilized to polymerize olefins and at least one activator or, alternatively, at least one cocatalyst. The catalyst composition may include any suitable number of catalyst compounds in any combination as described herein, as well as any activator or cocatalyst in any combination as described herein.

As used herein, a "supported catalyst composition" includes one or more catalyst compounds utilized to polymerize olefins and at least one activator or, alternatively, at least one cocatalyst, and at least one support. The supported catalyst composition may include any suitable number of catalyst compounds in any combination as described herein, as well as any activator or cocatalyst in any combination as described herein. A "supported catalyst composition" may also contain one or more additional components known in the art to reduce or eliminate reactor fouling such as continuity additives.

As used herein, a "catalyst compound" may include any compound that, when activated, is capable of catalyzing the polymerization or oligomerization of olefins, wherein the catalyst compound comprises at least one Group 3 to 12 atom, and optionally at least one leaving group bound thereto.

The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, iso-butyl, t-butyl, octyl, decyl, and the like, as well as cycloalkyl groups such as cyclopentyl, cyclohexyl and the like. Generally, although again not necessarily, alkyl groups herein may contain 1 to about 12 carbon atoms. The term "lower alkyl" intends an alkyl group of one to six carbon atoms, specifically one to four carbon atoms. "Substituted alkyl" refers to alkyl substituted with one or more substituent groups (e.g., benzyl or chloromethyl), and the terms "heteroatom-containing alkyl" and "heteroalkyl" refer to alkyl in which at least one carbon atom is replaced with a heteroatom (e.g., —$CH_2OCH_3$ is an example of a heteroalkyl).

The term "alkenyl" as used herein refers to a branched or unbranched hydrocarbon group typically although not necessarily containing 2 to about 50 carbon atoms and at least one double bond, such as ethenyl, n-propenyl, iso-propenyl, n-butenyl, iso-butenyl, octenyl, decenyl, and the like. Generally, although again not necessarily, alkenyl groups herein contain 2 to about 12 carbon atoms. The term "lower alkenyl" refers to an alkenyl group of two to six carbon atoms, specifically two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 50 carbon atoms and at least one triple bond, such as ethynyl, n-propynyl, iso-propynyl, n-butynyl, isobutynyl, octynyl, decynyl, and the like. Generally, although again not necessarily, alkynyl groups herein may have 2 to about 12 carbon atoms. The term "lower alkynyl" refers to an alkynyl group of two to six carbon atoms, specifically three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group refers to an alkoxy group having one to six, more specifically one to four, carbon atoms. The term "aryloxy" is used in a similar fashion, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. A "lower alkyl thio" group refers to an alkyl thio group having one to six, more specifically one to four, carbon atoms. The term "arylthio" is used similarly, with aryl as defined below. The term "thioxy" refers to —SH.

The term "allenyl" is used herein in the conventional sense to refer to a molecular segment having the structure —CH=C=$CH_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. The aryl substituents may have 1 to about 200 carbon atoms, typically 1 to about 50 carbon atoms, and specifically 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom (e.g., rings such as thiophene, pyridine, isoxazole, pyrazole, pyrrole, furan, etc. or benzo-fused analogues of these rings are included in the term "heteroaryl"). In some embodiments herein, multi-ring moieties are substituents and in such an embodiment the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus, boron or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to hydrocarbyl radicals containing 1 to about 50 carbon atoms, specifically 1 to about 24 carbon atoms, most specifically 1 to about 16 carbon atoms, including branched or unbranched, saturated or unsaturated species, such as alkyl groups, alkenyl groups, aryl groups, and the like. The term "lower hydrocarbyl" refers to a hydrocarbyl group of one to six carbon atoms, specifically one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," "substituted alkenyl" and the like, as alluded to in some of the aforementioned definitions, is meant that in the hydrocarbyl, hydrocarbylene, alkyl, alkenyl, aryl or other moiety, at least one hydrogen atom bound to a carbon atom is replaced with one or more substituents that are functional groups such as hydroxyl, alkoxy, alkylthio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds. The term "aromatic" is used in its usual sense, including unsaturation that is essentially delocalized across multiple bonds, such as around a ring.

As used herein the term "silyl" refers to the —SiZ$^1$Z$^2$Z$^3$ radical, where each of Z$^1$, Z$^2$, and Z$^3$ is independently selected from the group consisting of hydride and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the —BZ$^1$Z$^2$ group, where each of Z$^1$ and Z$^2$ is as defined above.

As used herein, the term "phosphino" refers to the group —PZ$^1$Z$^2$, where each of Z$^1$ and Z$^2$ is as defined above. As used herein, the term "phosphine" refers to the group PZ$^1$Z$^2$Z$^3$, where each of Z$^1$, Z$^2$ and Z$^3$ is as defined above. The term "amino" is used herein to refer to the group —NZ$^1$Z$^2$, where each of Z$^1$ and Z$^2$ is as defined above. The term "amine" is used herein to refer to the group NZ$^1$Z$^2$Z$^3$, where each of Z$^1$, Z$^2$ and Z$^3$ is as defined above.

The term "saturated" refers to lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, acetylide, oxazolinyl, cyclohexenyl, acetyl and the like.

Other abbreviations used herein include: "iPr" to refer to isopropyl; "tBu" to refer to tertbutyl; "Me" to refer to methyl; "Et" to refer to ethyl; and "Ph" refers to phenyl.

The bridged bi-aromatic ligands disclosed herein have the following general formula (I):

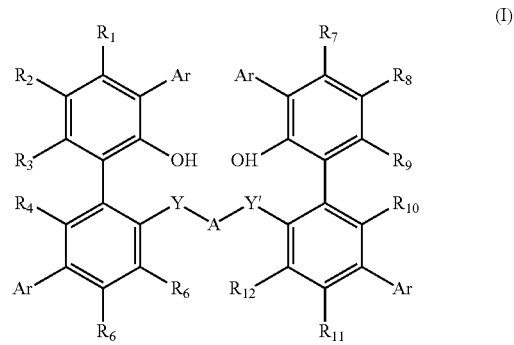

wherein each of R$^1$, R$^2$, R$^3$, R$^4$, R$^5$, R$^6$, R$^7$, R$^8$, R$^9$, R$^{10}$, R$^{11}$ and R$^{12}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is a bridging group having from one to 50 non-hydrogen atoms; Y and Y' are independently selected from O, S, NR$^a$ and PR$^a$ wherein R$^a$ is optionally substituted hydrocarbyl; Ar is, independently, optionally substituted aryl or optionally substituted heteroaryl.

The ligands may also have the following formula (II):

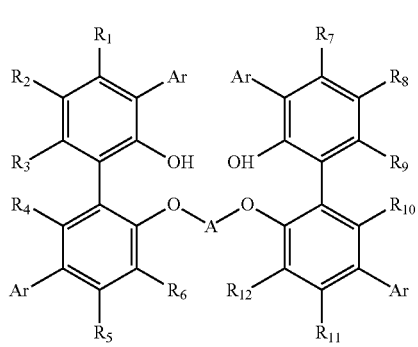

wherein each of $R^1$, $R^2$, $R^3$, $R^4$, $R^5$, $R^6$, $R^7$, $R^8$, $R^9$, $R^{10}$, $R^{11}$ and $R^{12}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is a bridging group having from one to 50 non-hydrogen atoms; Ar is, independently, optionally substituted aryl or optionally substituted heteroaryl.

Each of $R^1$, $R^2$, $R^3$, $R^4$, $R^5$, $R^6$, $R^7$, $R^8$, $R^9$, $R^{10}$, $R^{11}$ and $R^{12}$ may be hydride or optionally substituted alkyl or aryl. $R^2$ and $R^8$ may be optionally substituted alkyl and each of $R^1$, $R^3$, $R^4$, $R^5$, $R^6$, $R^7$, $R^9$, $R^{10}$, $R^{11}$ and $R^{12}$ may be hydride.

The bridging group A may be optionally substituted alkyl.

Ar may be optionally substituted phenyl, naphthyl, biphenyl, anthracenyl, phenanthrenyl or optionally substituted thiophene, pyridine, isoxazole, pyrazole, pyrrole, furan, etc. or benzo-fused analogues. The optional substituents may be alkyl groups.

The ligands may have the following structure:

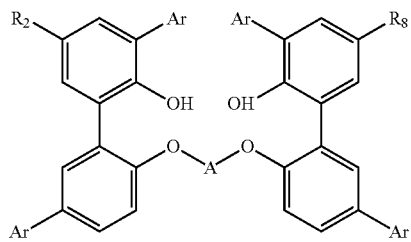

wherein Ar may be optionally substituted phenyl, naphthyl, biphenyl, anthracenyl, phenanthrenyl or optionally substituted thiophene, pyridine, isoxazole, pyrazole, pyrrole, furan, or benzo-fused analogues and the bridging group A is a divalent alkyl.

$R_2$ and $R_8$ may be optionally substituted alkyl.

The ligands may have the following structure:

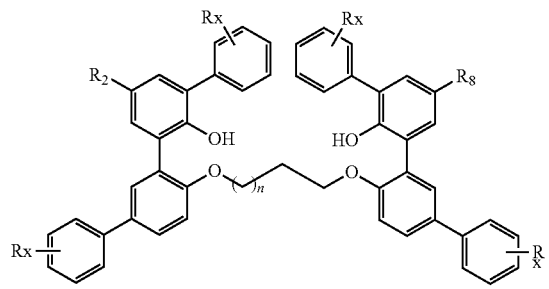

wherein Rx, $R_2$ and $R_8$ are alkyl, and n=0 to 6.

Specific ligands disclosed herein include:

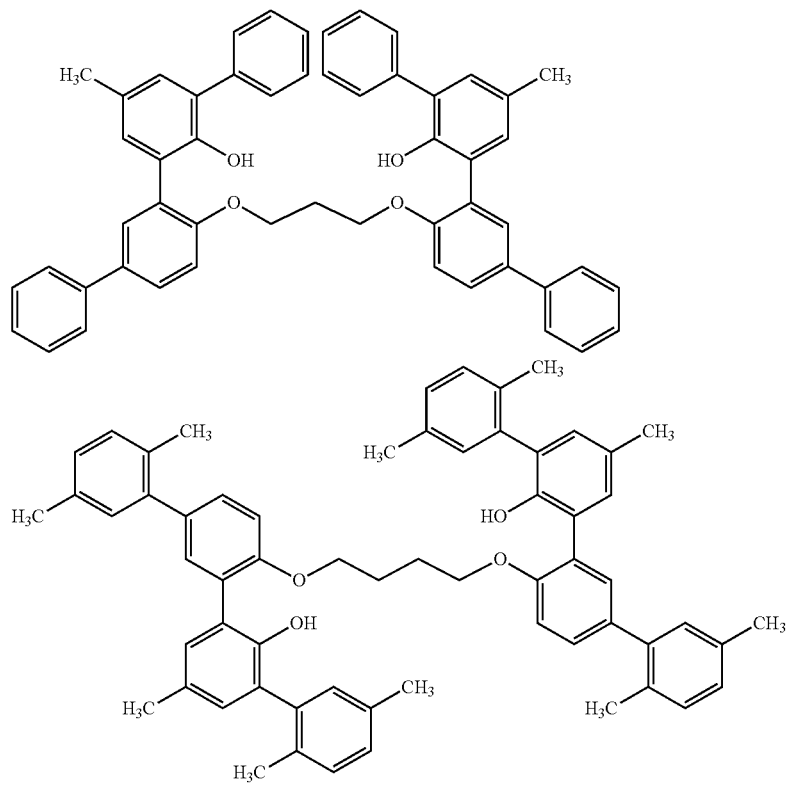

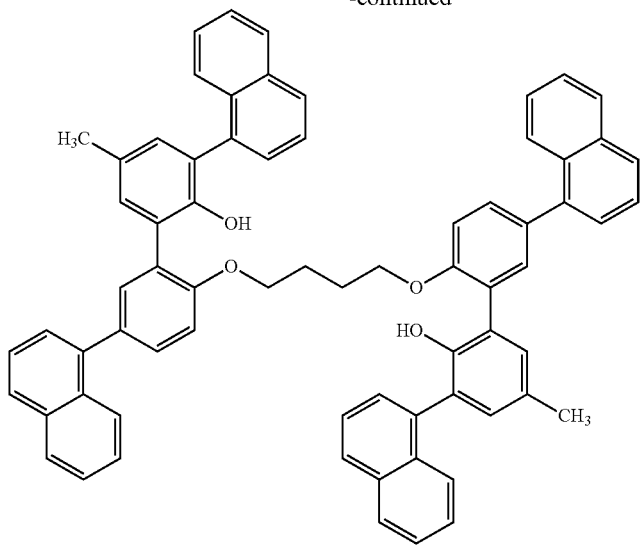

Ligand Synthesis

The ligands disclosed herein may be prepared by a variety of methods. In general the ligands may be prepared by employing a tetrabromination of a bridged phenyl phenol and aryl coupling. The aryl coupling may be Suzuki coupling and/or Negishi coupling.

A major advantage of the herein disclosed methods is that the number of reaction steps to access the ligands is low. For example, the disclosed ligands may be prepared from a bromophenol in three or four reaction steps.

Bridged bi-aromatic ligand syntheses disclosed in WO 03/09162 suffer from an abundance of synthetic steps which add time and cost to a synthesis. Suzuki couplings disclosed in WO 03/091162 were performed on protected phenols (THP, Bn, MOM, etc), which add steps due to the required protections and deprotections. However, given the protic solvents used in these reactions, it was hypothesized that a free phenol would not interfere with coupling. Indeed, a Suzuki coupling with bromocresol and phenyl boronic acid was successful and high yielding. Other boronic acids were also coupled to bromocresol without difficulty as shown below:

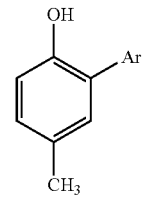

| Aryl group | Yield |
|---|---|
| Phenyl (1) | 81% |
| 2-methylphenyl (2) | 75% |
| 2,5-dimethylphenyl (3) | 75% |
| 3,5-dimethylphenyl (4) | 80% |
| Napthyl (5) | 77% |
| 2-methylnapthyl* (6) | 49% |

*pinacol borane

The following schemes illustrate general methods for the preparation of the ligands.

Schemes 1 and 2 illustrate Suzuki coupling of a brominated phenol with a bridged diboronic acid.

Scheme 1

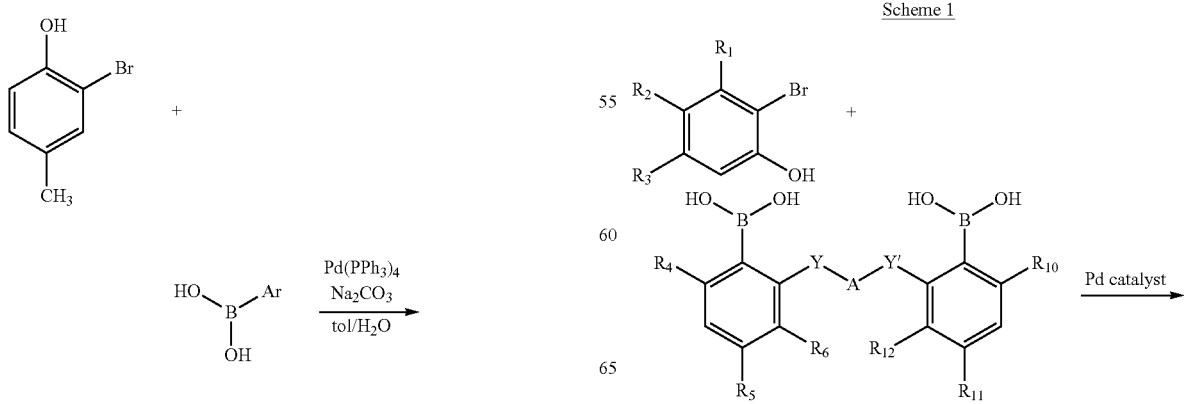

-continued
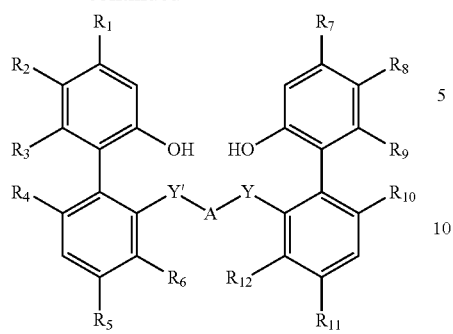
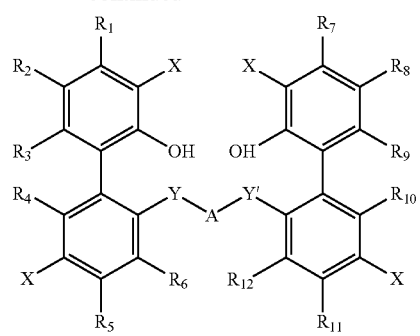
Scheme 2
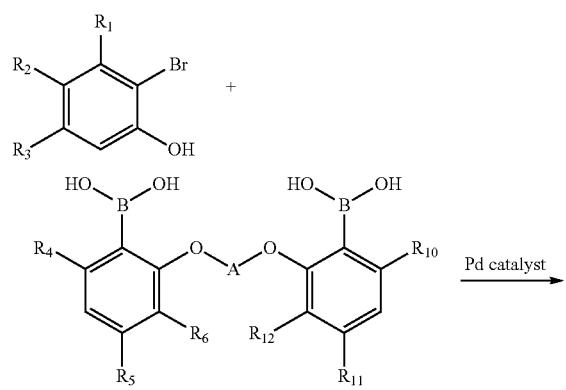
Schemes 3 and 4 illustrate tetrahalogenation of a bridged bi-aromatic phenol.
Schemes 5 and 6 illustrate Suzuki coupling of the tetrahalogenated phenols with aryl boronic acid.
Scheme 3
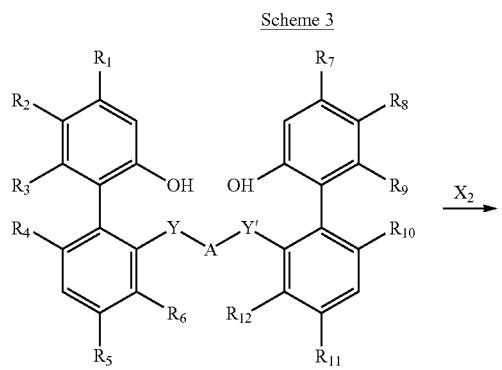
Scheme 4
Scheme 5
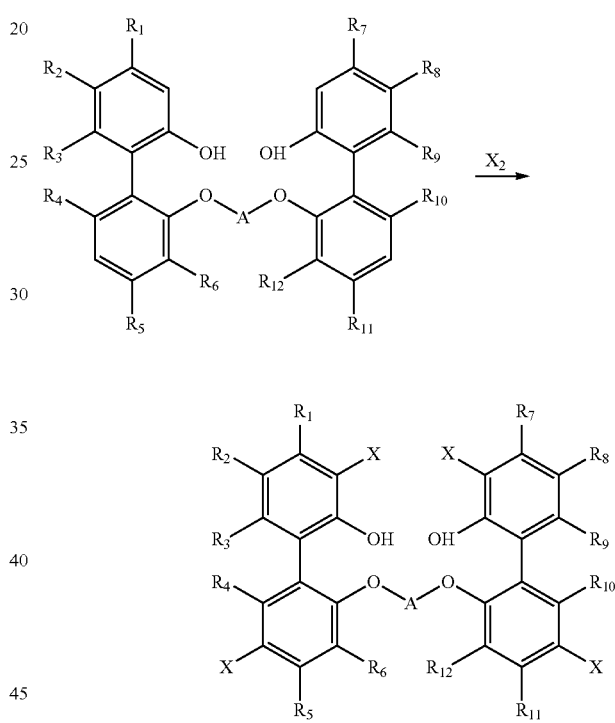
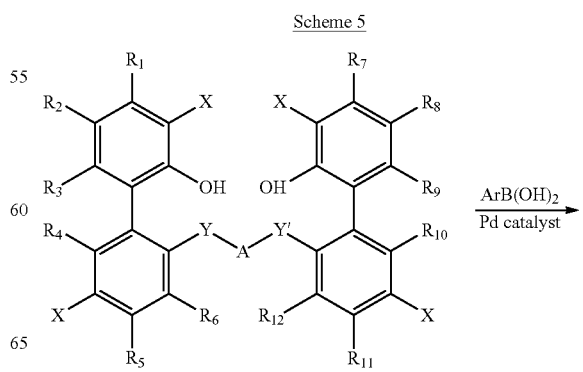

-continued

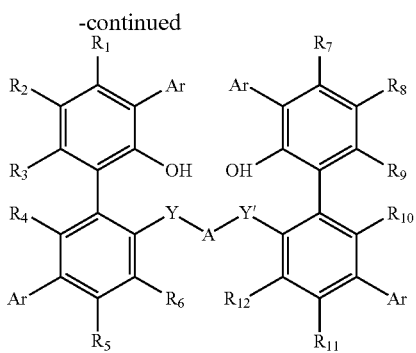

Scheme 6

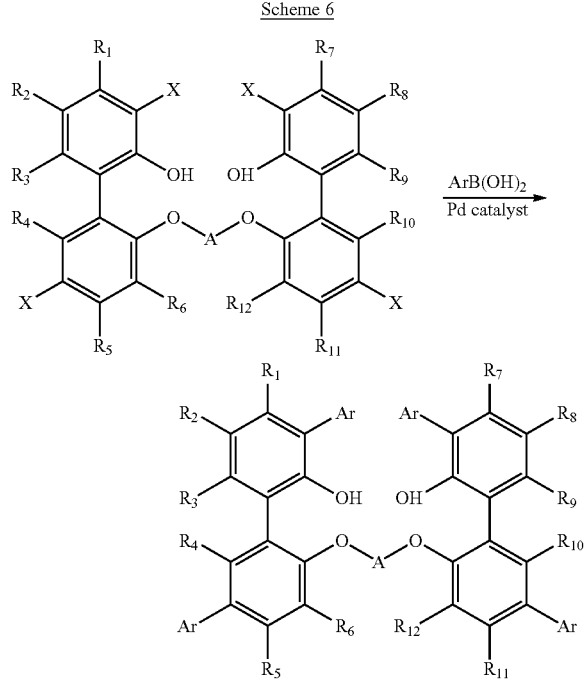

In any one of the above methods each of $R^1$, $R^2$, $R^3$, $R^4$, $R^5$, $R^6$, $R^7$, $R^8$, $R^9$, $R^{10}$, $R^{11}$ and $R^{12}$ may be independently selected from the group consisting of hydride and optionally substituted alkyl or aryl.

In any of the above methods Y and Y' may be O.

In any of the above methods A may be selected from the group consisting of optionally substituted divalent alkyl, alkenyl, alkynyl, heteroalkyl, heteroalkenyl, heteroalkynyl, carbocycle, heterocarbocycle, aryl, heteroaryl and silyl.

In any of the above methods A may be optionally substituted alkyl.

In any of the above methods the palladium catalyst may comprise a palladium phosphine compound, for example, bis(tri-tert-butylphosphine)palladium (Pd(PPh$_3$)$_4$), tetrakis(triphenylphosphine)palladium(0) (Pd(dppe)$_2$), bis[1,2-bis(diphenylphosphino)ethane]palladium(0) (Pd(dppf)), 1,1'-bis(diphenylphosphino)ferrocene palladium, (2,2'-bis(diphenylphosphino)-1,1'-binaphthyl palladium (Pd (BINAP).

In any of the above methods the palladium catalyst may comprise a palladium compound and one or more phosphines. For example, tris(dibenzylideneacetone)dipalladium (0) (Pd$_2$(dba)$_3$) and Pd(OAc)$_2$ and one or more phosphine compounds.

In any of the above methods X may be bromo or chloro. The source of halogen may be bromine or chlorine.

In any of the above methods the Ar-boron compound may be an optionally substituted aryl boronic acid or an optionally substituted heteroaryl boronic acid.

In any of the above methods the Ar-boron compound may be an optionally substituted aryl boronic ester or an optionally substituted heteroaryl boronic ester.

In any of the above methods the Ar-boron compound may be an optionally substituted aryl trifluoroborate or an optionally substituted heteroaryl trifluoroborate.

In any of the above methods the Ar-boron compound may be an optionally substituted arylborane or an optionally substituted heteroarylborane.

In any of the above methods a base may be utilized along with the palladium catalyst.

In any of the above methods the base may comprise an alkali metal carbonate, alkali metal phosphate, alkali metal hydroxide, alkali metal alkoxide or an amine.

The base may comprise sodium or potassium carbonate or sodium or potassium phosphate.

Figure 3:
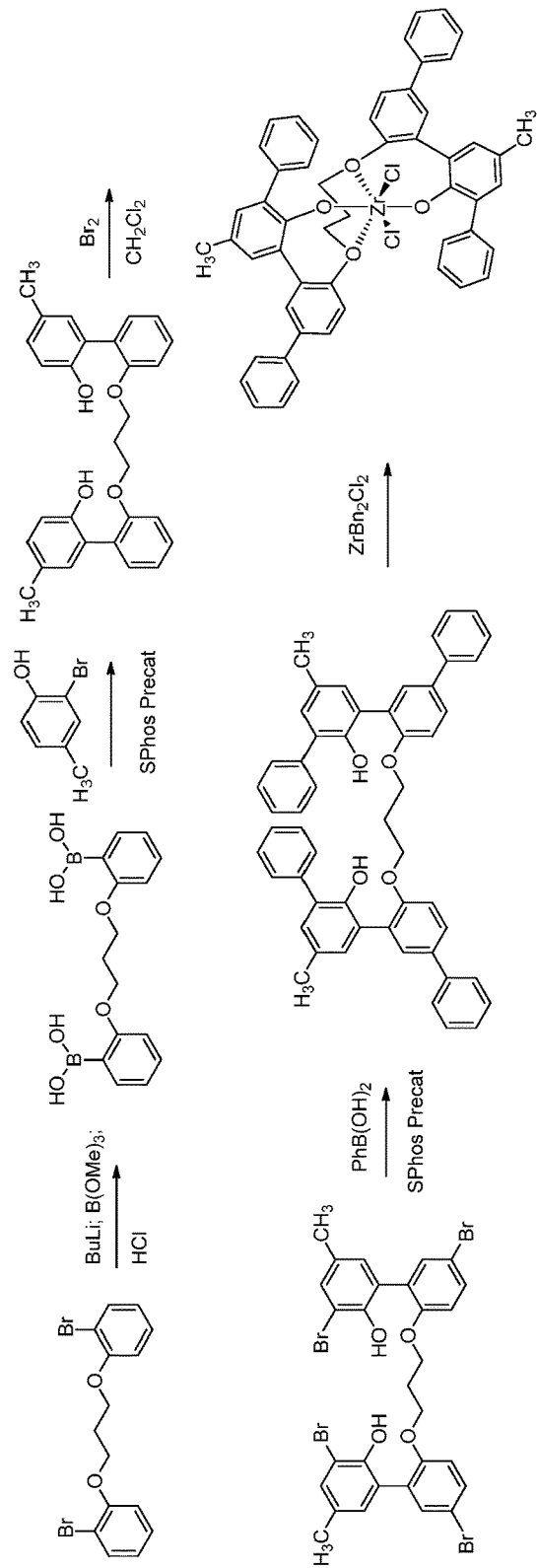
FIGS. 3 to 5 depict exemplary reaction schemes in accordance with the present disclosure.

In an illustrative embodiment and referring to the structures in FIG. 1 and the reaction scheme in FIG. 3: treatment of 1,3-bis(2-bromophenoxy)propane with n-butyllithium followed by trimethyl borate and then HCl afforded (Propane-1,3-diylbisoxy)bis(2,1-phenylene)diboronic acid (9). The diboronic acid, 2-bromocresol, SPhos, and potassium phosphate were dissolved in degassed THF and water, then stirred at ambient temperature overnight to yield 2',2'''-(Propane-1,3-diylbis(oxy))bis(5-methyl-[1,1'-biphenyl]-2-ol) (10). The diphenolic compound (10) was dissolved in dichloromethane and treated with bromine. The reaction was quenched with saturated sodium bicarbonate to yield 6',6'''-(Propane-1,3-diylbisoxy)bis(3,3'-dibromo-5-methyl-[1,1'-biphenyl]-2-ol) (11). The brominated compound was combined with phenylboronic acid, SPhos and potassium phosphate in THF/H$_2$O and the mixture was stirred at room temperature overnight to yield 6'',6''''''-(Propane-1,3-diylbisoxy)bis(5'-methyl-[1,1':3',1'',1'''-quaterphenyl]-2'-ol) (12).

Figure 4:
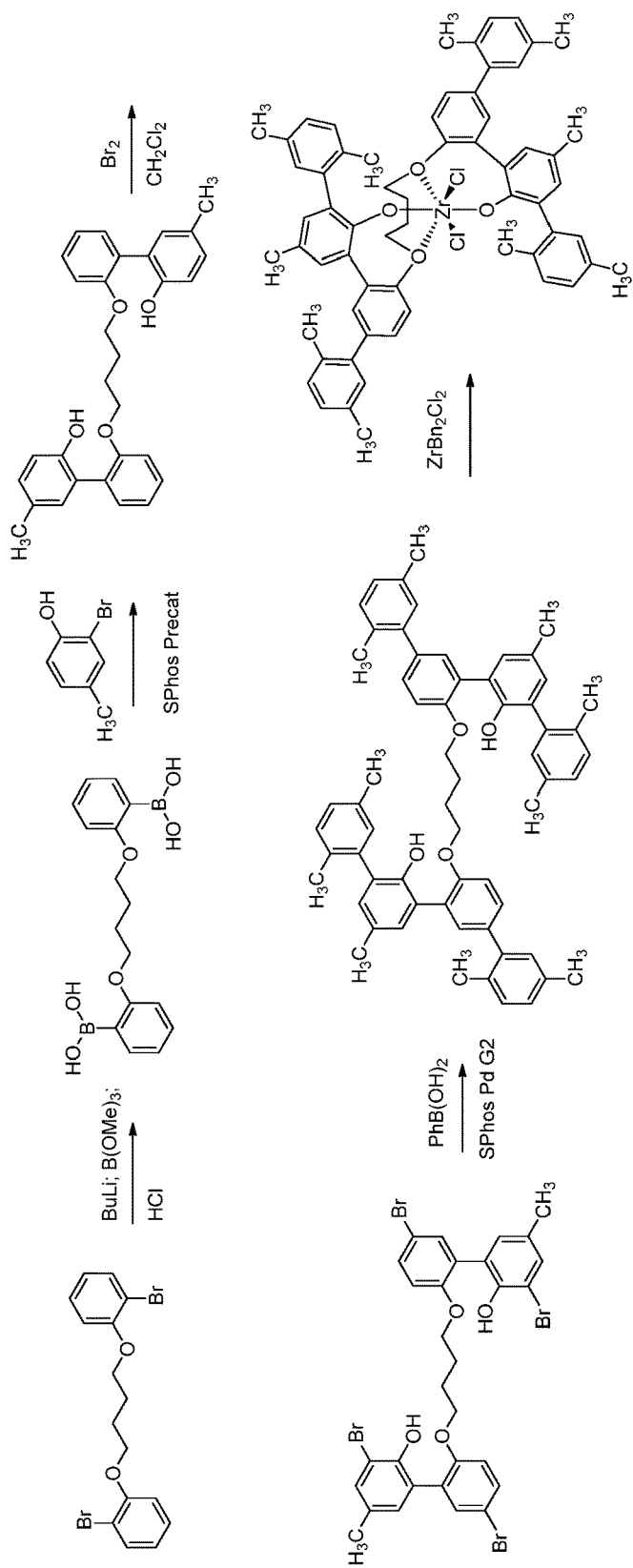
Figure 5:
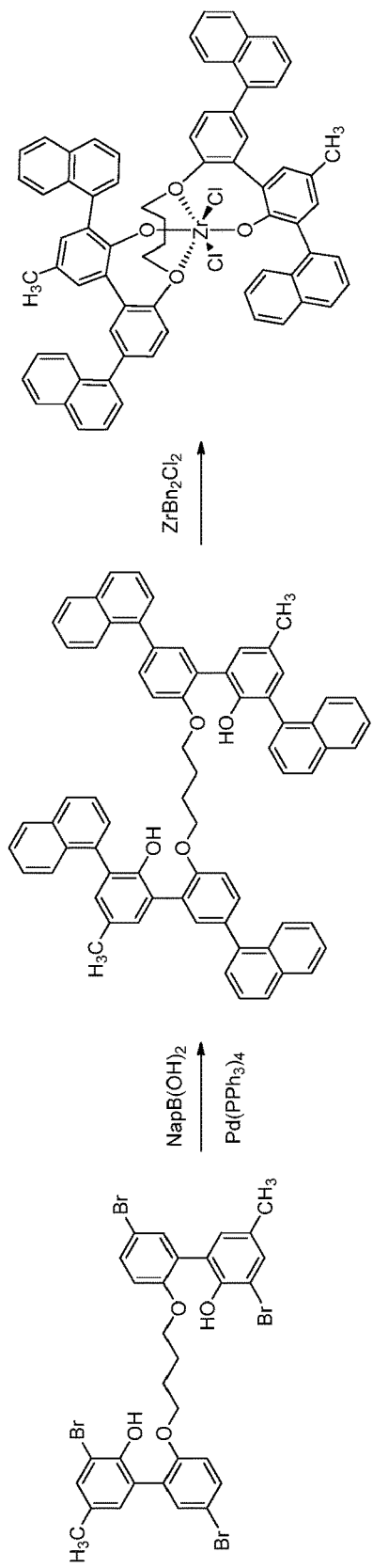

FIGS. 4 and 5 illustrate other exemplary reaction schemes.

Catalyst Compounds

The catalyst compounds may be prepared by any suitable synthesis method and the method of synthesis is not critical to the present disclosure. One useful method of preparing the catalyst compounds of the present disclosure is by reacting a suitable metal compound, for example one having a displaceable anionic ligand, with the bridged bi-aromatic ligands of this disclosure. Non-limiting examples of suitable metal compounds include organometallics, metal halids, sulfonates, carboxylates, phosphates, organoborates (including fluoro-containing and other subclasses), acetonacetonates, sulfides, sulfates, tetrafluoroborates, nitrates, perchlorates, phenoxides, alkoxides, silicates, arsenates, borohydrides, naphthenates, cyclooctadienes, diene conjugated complexes, thiocynates, cyanates, and the metal cyanides. The metal compound may be an organometallic or metal halide. The metal compound may be an organometallic.

The metal of the organometallic compound may be selected from Groups 1 to 16, or a transition metal selected from Groups 3 to 13 elements and Lanthanide series elements. The metal may be selected from Groups 3 to 7 elements. The metal may be a Group 4 metal, titanium, zirconium or hafnium.

The metal compound can, for example, be a metal hydrocarbyl such as: a metal alkyl, a metal aryl, a metal arylalkyl; a metal silylalkyl; a metal diene, a metal amide; or a metal phosphide. The metal compound may be a zirconium or hafnium hydrocarbyl. The transition metal compound may be a zirconium arylalkyl.

An exemplary reaction is shown below:

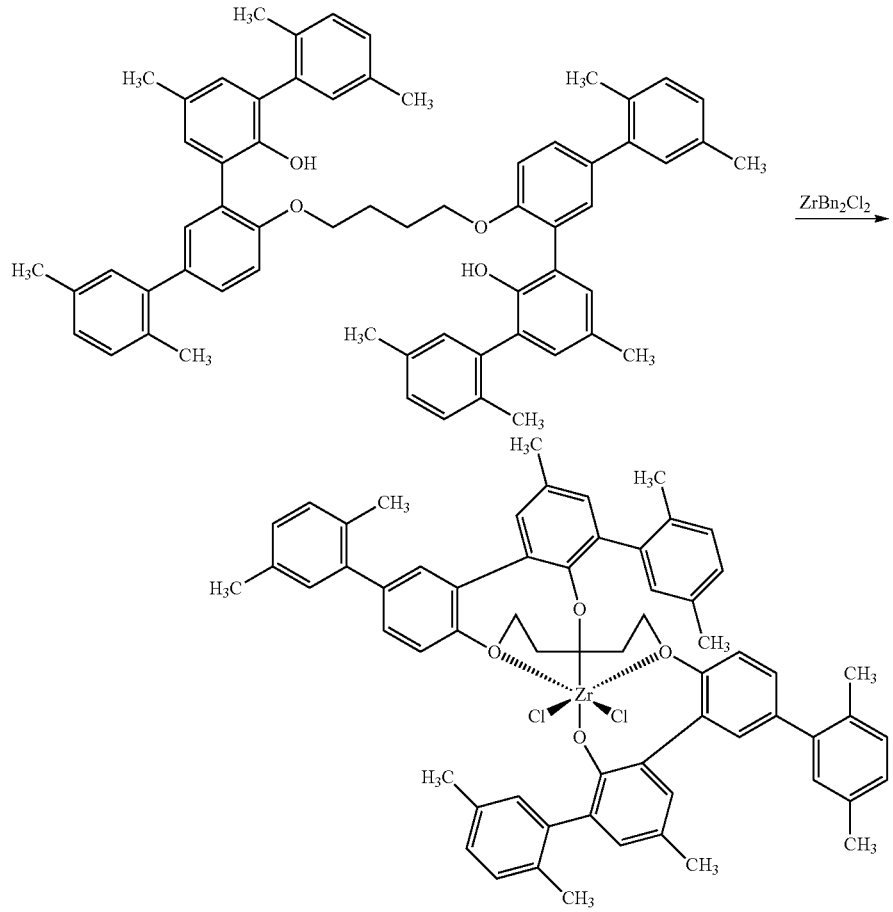

Examples of useful and preferred metal compounds include:
(i) tetramethylzirconium, tetraethylzirconium, zirconiumdichloride ($\eta^4$-1,4-diphenyl-1,3-butadiene), bis (triethylphosphine) and zirconiumdichloride ($\eta^4$-1,4-diphenyl-1,3-butadiene) bis (tri-n-propylphosphine), tetrakis[trimethylsilylmethyl]zirconium, tetrakis[dimethylamino]zirconium, dichlorodibenzylzirconium, chlorotribenzylzirconium, trichlorobenzylzirconium, bis[dimethylamino]bis[benzyl]zirconium, and tetrabenzylzirconium;
(ii) tetramethyltitanium, tetraethyltitanium, titaniumdichloride ($\eta^4$-1,4-diphenyl-1,3-butadiene), bis (triethylphosphine) and titaniumdichloride ($\eta^4$-1,4-diphenyl-1,3-butadiene) bis (tri-n-propylphosphine), tetrakis[trimethylsilylmethyl]titanium, tetrakis[dimethylamino]titanium, dichlorodibenzyltitanium, chlorotribenzyltitanium, trichlorobenzyltitanium, bis[dimethylamino]bis[benzyl]titanium, and tetrabenzyltitanium; and
(iii) tetramethylhafnium, tetraethylhafnium, hafniumdichloride ($\eta^4$-1,4-diphenyl-1,3-butadiene), bis (triethylphosphine) and hafniumdichloride ($\eta^4$-1,4-diphenyl-1,3-butadiene) bis (tri-n-propylphosphine), tetrakis[trimethylsilylmethyl]hafnium, tetrakis[dimethylamino]hafnium, dichlorodibenzylhafnium, chlorotribenzylhafnium, trichlorobenzylhafnium, bis[dimethylamino]bis[benzyl]hafnium, and tetrabenzylhafnium.

Catalyst and Supported Catalyst Compositions

The catalyst compositions disclosed herein may comprise one or more catalyst compounds as disclosed herein and one or more activators as disclosed herein.

The supported catalyst compositions as disclosed herein may comprise one or more supports as disclosed herein, one or more catalyst compounds as disclosed herein and one or more activators as disclosed herein.

The catalyst compositions and supported catalyst compositions may comprise one or more of the catalyst compounds as hereinbefore disclosed along with another catalyst compound, such as a metallocene catalyst compound or a Group V atom containing catalyst compound. Suitable other catalyst compounds include, but are not limited to:
(pentamethylcyclopentadienyl)(propylcyclopentadienyl)MX$_2$,
(tetramethylcyclopentadienyl)(propylcyclopentadienyl)MX$_2$,
(tetramethylcyclopentadienyl)(butylcyclopentadienyl)MX$_2$,
Me$_2$Si(indenyl)$_2$MX$_2$,
Me$_2$Si(tetrahydroindenyl)$_2$MX$_2$, (n-propyl cyclopentadienyl)$_2$MX$_2$,
(n-butyl cyclopentadienyl)$_2$MX$_2$,
(1-methyl, 3-butyl cyclopentadienyl)$_2$MX$_2$,
HN(CH$_2$CH$_2$N(2,4,6-Me$_3$phenyl))$_2$MX$_2$,
HN(CH$_2$CH$_2$N(2,3,4,5,6-Me$_5$phenyl))$_2$MX$_2$,
(propyl cyclopentadienyl)(tetramethylcyclopentadienyl) MX$_2$,
(butyl cyclopentadienyl)$_2$MX$_2$,
(propyl cyclopentadienyl)$_2$MX$_2$, and mixtures thereof, wherein M is Zr or Hf, and X is selected from F, Cl, Br, I, Me, benzyl, CH$_2$SiMe$_3$, and C$_1$ to C$_5$ alkyls or alkenyls.

The supported catalyst composition may in the form of a substantially dry powder or be in the form of a slurry in at least one liquid vehicle. Non-limiting examples of liquid vehicles include mineral oils, aromatic hydrocarbons or aliphatic hydrocarbons.

Activator Compounds

An activator is defined in a broad sense as any combination of reagents that increases the rate at which a transition metal compound oligomerizes or polymerizes unsaturated monomers, such as olefins. The catalyst compounds may be activated for oligomerization and/or polymerization catalysis in any manner sufficient to allow coordination or cationic oligomerization and/or polymerization.

Additionally, the activator may be a Lewis-base, such as for example, diethyl ether, dimethyl ether, ethanol, or methanol. Other activators that may be used include those described in WO 98/07515 such as tris (2,2',2"-nonafluorobiphenyl) fluoroaluminate.

Combinations of activators may be used. For example, alumoxanes and ionizing activators may be used in combinations, see for example, EP-B1 0 573 120, WO 94/07928 and WO 95/14044 and U.S. Pat. Nos. 5,153,157 and 5,453,410. WO 98/09996 describes activating metallocene catalyst compounds with perchlorates, periodates and iodates including their hydrates. WO 98/30602 and WO 98/30603 describe the use of lithium (2,2'-bisphenyl-ditrimethylsilicate).4THF as an activator for a metallocene catalyst compound. WO 99/18135 describes the use of organo-boron-aluminum activators. EP-B1-0 781 299 describes using a silylium salt in combination with a non-coordinating compatible anion. WO 2007/024773 suggests the use of activator-supports which may comprise a chemically-treated solid oxide, clay mineral, silicate mineral, or any combination thereof. Also, methods of activation such as using radiation (see EP-B1-0 615 981), electro-chemical oxidation, and the like are also contemplated as activating methods for the purposes of rendering the neutral metallocene catalyst compound or precursor to a metallocene cation capable of polymerizing olefins. Other activators or methods for activating a metallocene catalyst compound are described in, for example, U.S. Pat. Nos. 5,849,852, 5,859,653 and 5,869,723 and PCT WO 98/32775.

Alumoxanes may also be utilized as an activator in the catalyst composition. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in, for example, U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, WO 94/10180 and WO 99/15534. A visually clear methylalumoxane may be used. A cloudy or gelled alumoxane can be filtered to produce a clear solution or clear alumoxane can be decanted from the cloudy solution. Another alumoxane is a modified methyl alumoxane (MMAO) cocatalyst type 3A (commercially available from Akzo Chemicals, Inc. under the trade name Modified Methylalumoxane type 3A, disclosed in U.S. Pat. No. 5,041,584).

An ionizing or stoichiometric activator, neutral or ionic, such as tri (n-butyl) ammonium tetrakis (pentafluorophenyl) boron, a trisperfluorophenyl boron metalloid precursor or a trisperfluoronapthyl boron metalloid precursor, polyhalogenated heteroborane anions (see, for example, WO 98/43983), boric acid (see, for example, U.S. Pat. No. 5,942,459) or combinations thereof, may also be used. The neutral or ionic activators may be used alone or in combination with alumoxane or modified alumoxane activators.

Examples of neutral stoichiometric activators may include tri-substituted boron, tellurium, aluminum, gallium and indium or mixtures thereof. The three substituent groups may be each independently selected from the group of alkyls, alkenyls, halogen, substituted alkyls, aryls, arylhalides, alkoxy and halides. The three substituent groups may be independently selected from the group of halogen, mono or multicyclic (including halosubstituted) aryls, alkyls, and alkenyl compounds and mixtures thereof; or alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). Alternatively, the three groups are alkyls having 1 to 4 carbon groups, phenyl, napthyl or mixtures thereof. The three groups may be halogenated, for example fluorinated, aryl groups. In yet other illustrative examples, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in, for example, European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124.

Supports

The above described catalyst compounds may be combined with one or more supports using one of the support methods well known in the art or as described below. For example, the catalyst compound may be used in a supported form, such as, deposited on, contacted with, or incorporated within, adsorbed or absorbed in, or on the support.

As used herein, the term "support" refers to compounds comprising Group 2, 3, 4, 5, 13 and 14 oxides and chlorides. Suitable supports include, for example, silica, magnesia, titania, zirconia, montmorillonite, phyllosilicate, alumina, silica-alumina, silica-chromium, silica-titania, magnesium chloride, graphite, magnesia, titania, zirconia, montmorillonite, phyllosilicate, and the like.

The support may possess an average particle size in the range of from about 0.1 to about 500 µm, or from about 1 to about 200 µm, or from about 1 to about 50 µm, or from about 5 to about 50 µm.

The support may have an average pore size in the range of from about 10 to about 1000 Å, or about 50 to about 500 Å, or 75 to about 350 Å.

The support may have a surface area in the range of from about 10 to about 700 m$^2$/g, or from about 50 to about 500 m$^2$/g, or from about 100 to about 400 m$^2$/g.

The support may have a pore volume in the range of from about 0.1 to about 4.0 cc/g, or from about 0.5 to about 3.5 cc/g, or from about 0.8 to about 3.0 cc/g.

The support, such as an inorganic oxide, may have a surface area in the range of from about 10 to about 700 m$^2$/g, a pore volume in the range of from about 0.1 to about 4.0 cc/g, and an average particle size in the range of from about 1 to about 500 µm. Alternatively, the support may have a surface area in the range of from about 50 to about 500 m$^2$/g, a pore volume of from about 0.5 to about 3.5 cc/g, and an average particle size of from about 10 to about 200 µm. The surface area of the support may be in the range from about 100 to about 400 m$^2$/g, a pore volume of from about 0.8 to about 3.0 cc/g and an average particle size of from about 5 to about 100 µm.

The catalyst compounds may be supported on the same or separate supports together with an activator, or the activator may be used in an unsupported form, or may be deposited on a support different from the supported catalyst compound.

There are various other methods in the art for supporting a polymerization catalyst compound. For example, the catalyst compound may contain a polymer bound ligand as described in, for example, U.S. Pat. Nos. 5,473,202 and 5,770,755; the catalyst may be spray dried as described in, for example, U.S. Pat. No. 5,648,310; the support used with the catalyst may be functionalized as described in European publication EP-A-0 802 203, or at least one substituent or leaving group is selected as described in U.S. Pat. No. 5,688,880.

Polymerization Processes

Polymerization processes may include solution, gas phase, slurry phase and a high pressure process or a combination thereof. In illustrative embodiments, a gas phase or slurry phase polymerization of one or more olefins at least one of which is ethylene or propylene is provided. Optionally, the reactor is a gas phase fluidized bed polymerization reactor.

The catalyst compositions or supported catalyst compositions as hereinbefore described are suitable for use in any prepolymerization and/or polymerization process over a wide range of temperatures and pressures. The temperatures may be in the range of from −60° C. to about 280° C., from 50° C. to about 200° C.; from 60° C. to 120° C. from 70° C. to 100° C. or from 80° C. to 95° C.

The present process may be directed toward a solution, high pressure, slurry or gas phase polymerization process of one or more olefin monomers having from 2 to 30 carbon atoms, preferably 2 to 12 carbon atoms, and more preferably 2 to 8 carbon atoms. The process is particularly well suited to the polymerization of two or more olefins or comonomers such as ethylene, propylene, 1-butene, 1-pentene, 4-methyl-1-pentene, 1-hexene, 1-octene 1-decene or the like.

Other olefins useful in the present process include ethylenically unsaturated monomers, diolefins having 4 to 18 carbon atoms, conjugated or nonconjugated dienes, polyenes, vinyl monomers and cyclic olefins. Useful monomers may include, but are not limited to, norbornene, norbornadiene, isobutylene, isoprene, vinylbenzocyclobutane, styrenes, alkyl substituted styrene, ethylidene norbornene, dicyclopentadiene and cyclopentene. In an illustrative embodiment of the present process, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process. In another embodiment of the present process, ethylene or propylene is polymerized with at least two different comonomers, optionally one of which may be a diene, to form a terpolymer.

The present process may be directed to a polymerization process, particularly a gas phase or slurry phase process, for polymerizing propylene alone or with one or more other monomers including ethylene, and/or other olefins having from 4 to 12 carbon atoms. The polymerization process may comprise contacting ethylene and optionally an alpha-olefin with one or more of the catalyst compositions or supported catalyst compositions as hereinbefore described in a reactor under polymerization conditions to produce the ethylene polymer or copolymer.

Suitable gas phase polymerization processes are described in, for example, U.S. Pat. Nos. 4,543,399, 4,588,790, 5,028,670, 5,317,036, 5,352,749, 5,405,922, 5,436,304, 5,453,471, 5,462,999, 5,616,661, 5,668,228, 5,627,242, 5,665,818, and 5,677,375, and European publications EP-A-0 794 200, EP-A-0 802 202, EP-A2 0 891 990, and EP-B-634 421.

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization process is referred to as a particle form polymerization, or a slurry process where the temperature is kept below the temperature at which the polymer goes into solution. Such technique is well known in the art, and described in for instance U.S. Pat. No. 3,248,179. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484. Examples of solution processes are described in U.S. Pat. Nos. 4,271,060, 5,001,205, 5,236,998 and 5,589,555.

EXAMPLES

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the following examples are put forth so as to provide those skilled in the art with a complete disclosure and description of how to make and use the disclosed compositions, and are not intended to limit the scope of the disclosure.

General:

All reagents were purchased from commercial vendors and used as received unless otherwise noted. Analytical thin-layer chromatography (TLC) was performed on Selecto Plates (200 μm) precoated with a fluorescent indicator. Visualization was effected using ultraviolet light (254 nm). Flash column chromatography was carried out with Sigma Aldrich Silica gel 60 Å (70-230 Mesh). NMR spectra were recorded on a Bruker 400 NMR with chemical shifts referenced to residual solvent peaks (CDCl$_3$: 7.27 ppm for $^1$H, 77.29 ppm for $^{13}$C; C$_6$D$_6$: 7.15 ppm for $^1$H, 77.39 ppm for $^{13}$C). Melting points are reported uncorrected. Abbreviations: SPhos-Chloro(2-dicyclohexylphosphino-2',6'-dimethoxy-1,1'-biphenyl)[2-(2'-amino-1,1'-biphenyl)]palladium (II); PTSA—para-toluenesulfonic acid.

General Procedure for Suzuki Coupling:

In an appropriately sized flask, 2-Bromo-p-cresol (1 equiv), aryl boronic acid (1.5 equiv) and palladium tetrakistriphenylphosphine (0.02 equiv) were dissolved in degassed toluene to make a 0.2 M solution with respect to the cresol. A 2 M solution of sodium carbonate (4 equiv) in degassed H$_2$O:MeOH (4:1) was added and the mixture refluxed until completion (usually overnight). The reaction was cooled and the layers separated. The aqueous layer was extracted twice with ethyl acetate and combined organic layers were washed with brine, dried over MgSO$_4$ or Na$_2$SO$_4$, filtered, and concentrated under reduced pressure.

5-Methyl-[1,1'-biphenyl]-2-ol (1)

Using the above general procedure, a white solid was isolated by column chromatography in 81% yield: $^1$H NMR (400 MHz, C$_6$D$_6$, δ): 2.10 (s, 3H), 6.69 (m, 3H), 7.12 (m, 2H), 7.15 (m, 1H), 7.35 (m, 2H).

2',5-Dimethyl-[1,1'-biphenyl]-2-ol (2)

Using the above general procedure, a white solid was isolated by column chromatography (30:70 actone:isohexane) in 75% yield: R$_f$=0.25 (30:70 acetone:isohexane); $^1$H NMR (400 MHz, CDCl$_3$, δ): 2.20 (s, 3H), 2.33 (s, 3H), 4.65 (br s, 1H), 6.70 (d, J=6.8 Hz, 1H), 6.94 (s, 1H), 7.10 (m, 1H), 7.33 (m, 4H).

3',5'-Trimethyl-[1,1'-biphenyl]-2-ol (3)

Using the above general procedure, a white solid was isolated by column chromatography (30:70 actone:isohexane) in 75% yield: R$_f$=0.32 (20:80 acetone:isohexane);
$^1$H NMR (400 MHz, CDCl$_3$, δ): 2.34 (s, 3H), 2.41 (s, 6H), 5.19 (br s, 1H), 6.91 (d, J=8.4 Hz, 1H), 7.08 (m, 5H).

2',5,5'-Trimethyl-[1,1'-biphenyl]-2-ol (4)

Using the above general procedure, a white solid was isolated by column chromatography (10% actone/isohexane) in 80% yield: R$_f$=0.26 (10:90 acetoneisohexane); $^1$H NMR (400 MHz, CDCl$_3$, δ): 2.15 (s, 3H), 2.32 (s, 3H), 2.36 (s, 3H), 4.66 (br s, 1H), 6.89 (d, J=8.4 Hz, 1H), 6.93 (m, 1H), 7.07 (m, 2H), 7.21 (m, 1H), 7.26 (m, 1H).

4-Methyl-2-(naphthalen-1-yl)phenol (5)

Using the above general procedure, the product was isolated by column chromatography (30% actone:isohexane) in 77% yield as a pale yellow oil: $^1$H NMR (500 MHz, CDCl$_3$, δ): 2.37 (s, 3H), 4.67 (s, 1H), 6.98 (d, J=9 Hz, 1H), 7.09 (s, 1H), 7.09 (m, 1H), 7.56 (m, 4H), 7.70 (d, J=8 Hz, 1H), 7.93 (m, 2H); $^{13}$C NMR (100 MHz, CDCl$_3$, δ): 20.8, 115.6, 126.0-134.5 (14 C), 151.2; IR (cm$^{-1}$): 3519, 3045, 2920, 1590, 1496, 1333, 1276, 1183, 781.

4-Methyl-2-(2-methylnaphthalen-1-yl)phenol (6)

Following the above general procedure, substituting 2-methylnapthyl pinacol borane for the aryl boronic acid, the product was purified by silica gel chromatography (10% acetone/isohexane) in 49% yield as a pale yellow oil which solidified upon standing. R$_f$=0.32 (30:70 acetone:isohexane); $^1$H NMR (400 MHz, CDCl$_3$, δ): 2.29 (s, 3H), 2.36 (s, 3H), 4.42 (s, 1H), 6.95 (s, 1H), 7.00 (d, J=4.0 Hz, 1H), 7.19 (d, J=8 Hz, 1H), 7.44 (m, 4H), 7.86 (t, J=8.0 Hz, 2H); $^{13}$C NMR (100 MHz, CDCl$_3$, δ): 20.7, 20.8, 115.4, 125.0, 125.5, 125.8, 126.8, 128.2, 128.7, 129.0, 130.1, 130.2, 131.5, 131.6, 132.5, 133.2, 135.8, 151.1; IR (cm$^{-1}$): 3498, 3426, 3050, 2922, 2860, 1617, 1594, 1497, 1335, 1275, 1228, 1188, 814.

3-Bromo-3',5,5'-trimethyl-[1,1'-biphenyl]-2-ol (7)

Phenol (3) (1 g, 4.7 mmol) was dissolved in methylene chloride and cooled to −35° C. Bromine (0.3 mL, 5.6 mmol) was slowly added and the solution stirred at ambient temperature overnight. The reaction was quenched with saturated sodium bicarbonate solution and extracted 3 times with methylene chloride. The combined organic portions were washed with sodium metabisulfite and brine, then dried over MgSO$_4$, filtered, and concentrated. R$_f$=0.30 (10:90 ethyl acetate:isohexane); $^1$H NMR (400 MHz, CDCl$_3$, δ): 2.33 (s, 3H), 2.49 (s, 6H), 5.07 (br s, 1H), 6.87 (d, J=8.4 Hz, 1H), 7.03 (m, 2H), 7.19 (s, 2H); $^{13}$C NMR (100 MHz, CDCl$_3$, δ): 24.7 (2 C), 25.2, 115.1, 127.4, 128.4, 129.1, 129.9, 130.3, 130.8, 131.6, 136.0, 139.4, 139.5, 150.3; IR (cm$^{-1}$): 3533, 2921, 1499, 1464, 1381, 1237, 1029, 814.

(Butane-1,4-diylbis(oxy))bis(2,1-phenylene)diboronic acid (8)

To 1,4-bis(2-bromophenoxy)butane (5 g, 12.5 mmol) dissolved in 40 mL THF, was added n-butyllithium (11 mL of 2.5 M). The reddish brown solution was stirred cold for 2 h. Trimethyl borate (5.6 mL, 50 mmol) was added as the solution slowly turned colorless and was stirred overnight at ambient temperature. The reaction was quenched with conc. HCl and condensed to a white solid. The solid was washed with ether to give the diboronic acid in 68% yield: $^1$H NMR (400 MHz, DMSO-d$_6$, δ): 1.92 (app br s, 4H), 4.10 (app br s, 4H), 6.93 (t, J=8.0 Hz, 2H), 7.00 (d, J=8.0 Hz, 2H), 7.36 (m, 2H), 7.55 (m, 2H), 7.72 (s, 4H).

(Propane-1,3-diylbisoxy)bis(2,1-phenylene)diboronic acid (9)

1,3-bis(2-bromophenoxy)propane (3.1 g, 8 mmol) was prepared according to established procedures and dissolved in 10 mL THF, then cooled to −70° C. n-Butyllithium (6.4 mL of 2.5 M) was added and the deep red reaction stirred for 1 h. Trimethyl borate (3.5 mL, 24 mmol) was added as the solution slowly turned colorless and warmed to ambient temperature over 1 h. The reaction was quenched with 10% HCl and extracted with three portions of ether. The combined organic layers were washed with brine, dried over Na$_2$SO$_4$, and concentrated. The product was recrystallized in dichloromethane, giving a white powder: $^1$H NMR (400 MHz, DMSO, δ): 2.25 (m, 2H), 4.19 (m, 4H), 6.93 (m, 2H), 6.99 (d, J=8.0 Hz, 2H), 7.36 (m, 2H), 7.53 (m, 2H), 7.74 (m, 2H); $^{13}$C NMR (100 MHz, DMSO-d$_6$, δ): 28.7, 64.1, 65.0, 111.2 (2 C), 114.5 (2 C), 120.5, 120.6, 131.5 (2 C), 138.4 (2 C).

2',2'''-(Propane-1,3-diylbis(oxy))bis(5-methyl-[1,1'-biphenyl]-2-ol) (10)

The above diboronic acid (600 mg, 1.89 mmol), 2-bromocresol (800 mg, 4.2 mmol), SPhos (50 mg, 0.07 mmol), and potassium phosphate (1.6 g, 7.56 mmol) were dissolved in degassed THF and water, then stirred at ambient temperature overnight. The reaction mixture was extracted with 4 portions of ether and the combined organic layers washed with brine, dried (Na$_2$SO$_4$), filtered and concentrated. Column chromatography (30% acetone/isohexane eluent) gave the cross-coupled product in 74% yield as a pale yellow oil: R$_f$=0.37 (acetone/isohexane 30:70); $^1$H NMR (400 MHz, CDCl$_3$, δ): 2.11 (qn, J=6.0 Hz, 2H), 2.33 (s, 6H), 4.10 (t, J=6.0 Hz, 4H), 6.02 (s, 2H), 6.91 (m, 4H), 7.05 (m, 2H), 7.14 (m, 4H), 7.35 (m, 4H); $^{13}$C NMR (100 MHz, CDCl$_3$, δ): 20.7 (2 C), 28.9, 65.8 (2 C), 113.5 (2 C), 117.0 (2 C), 122.6 (2 C), 126.0 (2 C), 127.7 (2 C), 129.4 (2 C), 129.9 (2 C), 130.1 (2 C), 131.8 (2 C), 132.4 (2 C), 151.5 (2 C), 154.9 (2 C); IR (cm$^{-1}$): 4307, 3028, 2923, 1597, 1499, 1445, 1270, 1229, 1113, 1054, 909, 818.

6',6'''-(Propane-1,3-diylbisoxy)bis(3,3'-dibromo-5-methyl-[1,1'-biphenyl]-2-ol) (11)

The above diphenolic compound (620 mg, 1.38 mmol) was dissolved in 40 mL dichloromethane. Bromine (0.178 mL, 3.47 mmol) was added slowly and the reaction stirred at room temperature for 1 h. The reaction was quenched with saturated sodium bicarbonate, and the organic layer washed with sodium metabisulfite and brine, then dried (Na$_2$SO$_4$), filtered and concentrated. The tetrabrominated compound was recrystallized in ether: $^1$H NMR (400 MHz, CDCl$_3$, δ): 2.05 (qn, J=6.0 Hz, 2H), 2.23 (s, 6H), 4.00 (t, J=6.0 Hz, 4H), 5.72 (s, 2H), 6.81 (d, J=8.0 Hz, 2H), 6.87 (d, J=4 Hz, 2H), 7.30 (d, J=4.0 Hz, 2H), 7.37 (d, J=4.0 Hz, 2H), 7.45 (m, 2H); $^{13}$C NMR (100 MHz, CDCl$_3$, δ): 20.5 (2 C), 28.6, 65.2 (2 C), 111.0 (2 C), 114.0 (2 C), 114.7 (2 C), 126.8 (2 C), 129.1 (2 C), 131.4 (4 C), 132.4 (2 C), 132.9 (2 C), 134.4 (2 C), 147.9 (2 C), 154.6 (2 C); IR (cm$^{-1}$): 3500, 2924, 1588, 1472, 1387, 1280, 1234, 1127, 1085, 808.

6'',6''''-(Propane-1,3-diylbisoxy)bis(5'-methyl-[1,1':3',1'':3',1'''-quaterphenyl]-2'-ol) (12)

The above brominated compound (420 mg, 0.55 mmol) was combined with phenylboronic acid (304 mg, 2.49 mmol), SPhos (40 mg, 0.055 mmol) and potassium phosphate (583 mg, 2.75 mmol) in 40 mL of degassed THF/H$_2$O. The mixture was stirred at room temperature overnight, and then extracted with 2 portions of ether. The combined organic layers were washed with brine, dried (Na$_2$SO$_4$), filtered and concentrated. The residue was purified by column chromatography giving the phenylated product as a pale yellow solid: mp=82-89° C.; R$_f$=0.44 (acetone/isohexane 30:70); $^1$H NMR (400 MHz, CD$_2$Cl$_2$, δ): 2.17 (m, 2H), 2.34 (s, 6H), 4.18 (t, J=8.0 Hz, 4H), 5.8 (s, 2H), $^{13}$C NMR (100 MHz, CD$_2$Cl$_2$, δ): 20.8 (2 C), 29.4, 65.9 (2 C), 113.7 (2 C), 127.0-131.7 (36 C), 135.3 (2 C), 139.3 (2 C), 140.8 (2 C), 148.7 (2 C), 155.3 (2 C).

Zr Complex (13)

The above diphenol (200 mg, 0.268 mmol) was dissolved in 15 mL toluene and cooled to −35° C. Dibenzylzirconium dichloride (105 mg, 0.268 mmol) was added and the reaction heated at 60° C. until a precipitate formed (approx. 3 h). Toluene was removed and the solid washed with hexane giving the zirconium complex as a pale cream colored powder: $^1$H NMR (400 MHz, CD$_2$Cl$_2$, δ): 1.53 (m, 2H), 2.34 (s, 3H), 2.38 (s, 3H), 3.76 (m, 2H), 4.15 (m, 2H), 7.14-7.89 (m, 30H).

2',2'''-(Butane-1,4-diylbisoxy)bis(5-methyl-[1,1-biphenyl]-2-ol) (14)

Diboronic acid (3 g, 9.1 mmol), 2-bromocresol (3.4 g, 18.1 mmol), SPhos (130 mg, 0.18 mmol), and potassium phosphate (7.7 g, 36 mmol) were dissolved in 200 mL THF/H$_2$O and stirred at ambient temperature overnight. The layers were separated and the aqueous layer extracted twice with ether. The combined organic layers were washed with 10% HCl and brine, then dried (Na$_2$SO$_4$), filtered and concentrated. The brown residue was purified by silica gel column chromatography (30% ethyl acetate/isohexane), giving the product as a pale yellow oil: $^1$H NMR (400 MHz, CDCl$_3$, δ): 1.81 (m, 4H), 2.31 (s, 6H), 3.98 (m, 4H), 6.22 (s, 2H), 6.88 (m, 4H), 7.03 (m, 4H), 7.32 (m, 4H); $^{13}$C NMR (100 MHz, CDCl$_3$, δ): 20.8 (2 C), 25.9 (2 C), 69.3 (2 C), 113.5 (2 C), 117.4 (2 C), 122.6 (2 C), 126.4 (2 C), 128.1 (2 C), 129.3 (2 C), 130.0 (2 C), 130.2 (2 C), 131.9 (2 C), 132.7 (2 C), 151.7 (2 C), 155.0 (2 C); IR (cm$^{-1}$): 3397, 3027, 2945, 1597, 1499, 1444, 1268, 1229, 1112, 818.

6',6'''-(Butane-1,4-diylbis(oxy))bis(3,3'-dibromo-5-methyl-[1,1-biphenyl]-2-ol) (15)

The above diphenolic compound (700 mg, 1.5 mmol) and triethylamine (0.30 mL, 2.2 mmol) were dissolved in 10 mL dichloromethane. Bromine (0.095 mL, 1.84 mmol) was added slowly and the reaction stirred at room temperature overnight. The reaction was quenched with saturated sodium bicarbonate, and the organic layer washed with sodium metabisulfite and brine, then dried (Na$_2$SO$_4$), filtered and concentrated. The resulting white powder was obtained in 95% yield by recrystallization from ether: $^1$H NMR (400 MHz, CDCl$_3$, δ): 1.75 (m, 4H), 2.27 (s, 6H), 3.93 (m, 4H), 5.99 (s, 2H), 6.79 (d, J=12.0 Hz, 2H), 6.94 (m, 2H), 7.40 (m, 2H), 7.45 (m, 4H); $^{13}$C NMR (125 MHz, CDCl$_3$, δ): 20.5 (2 C), 25.8 (2 C), 69.1 (2 C), 111.3 (2 C), 114.1 (2 C), 114.8 (2 C), 125.8 (2 C), 129.4 (2 C), 131.3 (2 C), 131.5 (2 C), 132.2 (2 C), 132.9 (2 C), 134.6 (2 C), 148.0 (2 C), 155.0 (2 C).

6'',6''''''-(Butane-1,4-diylbisoxy)bis(2,2''',5,5',5'''-pentamethyl-[1,1': 3',1'':3'',1'''-quaterphenyl]-2'-ol) (16)

The above brominated compound (700 mg, 0.908 mmol) was combined with 2,5-dimethylphenylboronic acid (613 mg, 4.1 mmol), SPhos (64 mg, 0.09 mmol) and potassium phosphate (1.5 g, 7.2 mmol) in 80 mL of degassed THF/$H_2O$. The mixture was stirred at room temperature overnight, and then extracted with 2 portions of ether. The combined organic layers were washed with brine, dried ($Na_2SO_4$), filtered and concentrated. The residue was purified by column chromatography giving the phenylated product as a pale yellow solid: $^1$H NMR (400 MHz, $CDCl_3$, δ): 1.83 (m, 4H), 2.16-2.36 (m, 30H), 4.03 (4H), 5.96 (s, 2H), 6.95 (m, 4H), 7.07 (m, 10H), 7.28 (m, 2H), 7.36 (m, 2H); $^{13}$C NMR (100 MHz, $CDCl_3$, δ): 20.4-23.5 (10 C), 26.7 (2 C), 69.8 (2 C), 113.5 (2 C), 118.2 (2 C), 126.9-141.8 (42 C), 149.2 (2 C), 154.9 (2 C); IR ($cm^{-1}$): 3539, 3384, 3015, 2920, 1609, 1493, 1461, 1382, 1228, 908, 811.

Zr complex (17)

To compound (16) (200 mg, 0.23 mmol) dissolved in 15 mL toluene, was added dibenzylzirconium dichloride (90 mg, 0.23 mmol) at −35° C. The mixture was heated at 70° C. for 3 h, then concentrated to an oil. Upon dissolving the oil in hexane, a while solid precipitated and was washed with pentane: $^1$H NMR (400 MHz, $CD_2Cl_2$, δ): 1.41 (m, 4H), 2.26-2.47 (m, 30H), 4.13 (m, 2H), 4.54 (m, 2H), 5.95 (d, J=8.0 Hz, 2H), 7.30 (m, 22H).

6',6'''-(Butane-1,4-diylbisoxy)bis(5-methyl-3,3'-di(naphthalen-1-yl)-[1,1-biphenyl]-2-ol) (18)

Brominated compound (15) (400 mg, 0.519 mmol) was combined with 2-naphthylboronic acid (402 mg, 2.3 mmol), palladium tetrakistriphenylphosphine (30 mg, 0.025 mmol) and sodium carbonate (770 mg, 7.26 mmol) in 20 mL of degassed tol/$H_2O$. The mixture was heated at 90° C. overnight, and then extracted with 2 portions of ether. The combined organic layers were washed with brine, dried ($Na_2SO_4$), filtered and concentrated. The residue was purified by column chromatography (20% acetone/isohexane) giving the tetranaphthylated product as a white powder in 52% yield: $^1$H NMR (400 MHz, $CDCl_3$, δ): 1.9 (m, 4H), 2.31 (s, 6H), 4.04 (m, 4H), 7.00 (m, 2H), 7.10 (m, 2H), 7.21 (m, 2H), 7.50 (m, 16H), 7.62 (m, 2H), 7.91 (m, 10H), 8.03 (d, J=12.4 Hz, 2H); $^{13}$C NMR (100 MHz, $CDCl_3$, δ): 20.7 (2 C), 23.1, 26.2, 69.3 (2 C), 112.9 (2 C), 125.6-134.4 (52 C), 134.8 (2 C), 137.1 (2 C), 139.8 (2 C), 149.3 (2 C), 154.7 (2 C); IR ($cm^{-1}$): 3393, 3043, 2950, 1710, 1600, 1497, 1465, 1226, 779.

Zr Complex (19)

Ligand (18) (200 mg, 0.208 mmol) was dissolved in 15 mL toluene and cooled to −35° C. Dibenzylzirconium dichloride (82 mg, 0.208 mmol) was added and the reaction heated at 90° C. until a precipitate formed (approx. 3 h). Toluene was removed and the solid washed with hexane giving the zirconium complex as a white powder: $^1$H NMR (500 MHz, tol-$d_8$, 90° C., δ): 1.64 (m, 4H), 2.12 (s, 3H), 2.17 (s, 3H), 3.72 (m, 4H), 5.51 (s, 1H), 6.78 (d, J=8.5 Hz, 2H), 7.06 (m, 2H), 7.30 (m, 19H), 7.64 (m, 10H), 7.87 (d, J=8.5 Hz, 2H), 8.06 (d, J=8.5 Hz, 2H).

General Procedure for Supporting Catalysts:

The zirconium complex, typically between 15 to 30 mg, was dissolved in toluene and a solution of methylalumoxane (MAO; Albemarle, 30 wt. % in toluene) added. Silica gel (Grace-Davison 757 pretreated at 600° C.) was added and the slurry stirred until completely mixed (approximately 5 minutes). Toluene was then removed under vacuum to give a dry free flowing powder.

Laboratory Polymerization Tests

A 2 L autoclave was charged with fine granular sodium chloride under an inert $N_2$ atmosphere. 5 g of methylalumoxane treated silica was added to the reactor by pressuring it in with a $N_2$ push. The reactor temperature was set to 85° C. The reactor was composed with hydrogen, 1-hexene and ethylene such that the set-point reactor pressure was 220 psig and the 1-hexene/ethylene mole ratio set. A pre-weighed charge of catalyst, between 10-15 mg, was pressured into the reactor. The pressure set-point of the reactor was set to 220 psig. Ethylene was fed to the reactor to maintain this set-point. $H_2$ and 1-hexene were also fed to the reactor such that their set-point concentration and $C_6/C_2$ ratio, respectively, were maintained. After one hour of run time, the polymer product was recovered and weighed.

The below Table collects the results of polymerization tests and polymer characterization:

| Zirconium Compound | C6/C2 Ratio | Productivity [g/g cat] | Mn | Mw | Mz | Mw/Mn | Recovery % | Me |
|---|---|---|---|---|---|---|---|---|
| (13) | 0.1000 | 2061 | 214020 | 642307 | 1414075 | 3.0 | 81.4 | 21.5 |
| (17) | 0.0800 | 3340 | 231817 | 776061 | 2055128 | 3.35 | 21.1 | 15.1 |
| (17) | 0.0150 | 1665 | 648027 | 1279746 | 2135760 | 1.97 | 100.8 | 2.2 |
| (19) | 0.1200 | 5182 | 292927 | 1039138 | 2703966 | 3.55 | 14 | 21.1 |
| (19) | 0.0200 | 3302 | 799696 | 1524295 | 2427565 | 1.91 | 49.6 | 4.1 |

All of the catalysts showed good productivity and made high molecular weight ethylene-1-hexene copolymers. 'Recovery %' refers to the % polymer recovered from the reactor. 'Me' refers to the number of short chain branch end groups as measured by NMR spectroscopy.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited are herein fully incorporated by reference for all jurisdictions in which such incorporation is permitted and to the extent such disclosure is consistent with the description of the present disclosure.

What is claimed is:

1. A bridged bi-aromatic phenol ligand of formula (I);

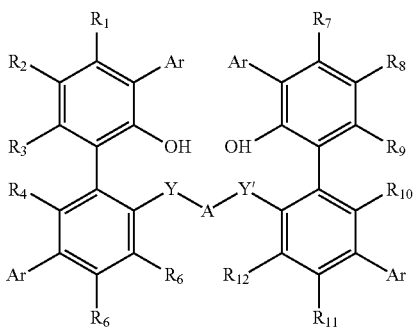

wherein each of $R^1$, $R^2$, $R^3$, $R^4$, $R^5$, $R^6$, $R^7$, $R^8$, $R^9$, $R^{10}$, $R^{11}$ and $R^{12}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is an optionally substituted divalent alkyl, alkenyl, alkynyl, heteroalkyl, heteroalkenyl, heteroalkynyl, carbocycle, heterocarbocycle, aryl, heteroaryl, or silyl; Y and Y' are independently selected from O, S, $NR^a$ and $PR^a$ wherein $R^a$ is optionally substituted hydrocarbyl; Ar is, independently, optionally substituted aryl or optionally substituted heteroaryl.

2. A bridged bi-aromatic phenol ligand according to claim 1 of formula (II):

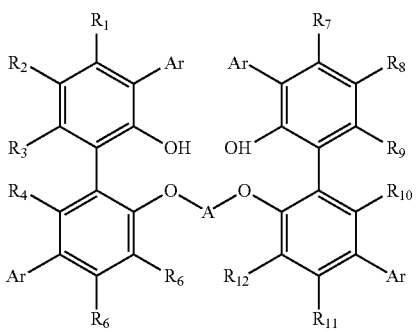

wherein each of $R^1$, $R^2$, $R^3$, $R^4$, $R^5$, $R^6$, $R^7$, $R^8$, $R^9$, $R^{10}$, $R^{11}$ and $R^{12}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is an optionally substituted divalent alkyl, alkenyl, alkynyl, heteroalkyl, heteroalkenyl, heteroalkynyl, carbocycle, heterocarbocycle, aryl, heteroaryl, or silyl; Ar is, independently, optionally substituted aryl or optionally substituted heteroaryl.

3. A bridged bi-aromatic phenol ligand according to claim 1 wherein $R^1$, $R^2$, $R^3$, $R^4$, $R^5$, $R^6$, $R^7$, $R^8$, $R^9$, $R^{10}$, $R^{11}$ and $R^{12}$ are independently selected from the group consisting of hydride, halide, and optionally substituted alkyl, heteroalkyl, aryl, heteroaryl, alkoxyl, aryloxyl, silyl, boryl, dialkylamino, alkylthio, arylthio, and seleno.

4. A bridged bi-aromatic phenol ligand according to claim 1 wherein $R^1$, $R^2$, $R^3$, $R^4$, $R^5$, $R^6$, $R^7$, $R^8$, $R^9$, $R^{10}$, $R^{11}$ and $R^{12}$ are independently selected from the group consisting of hydride, halide, and optionally substituted alkyl, heteroalkyl, aryl, heteroaryl, alkoxyl, and aryloxyl.

5. A bridged bi-aromatic phenol ligand according to claim 1 wherein $R^1$, $R^2$, $R^3$, $R^4$, $R^5$, $R^6$, $R^7$, $R^8$, $R^9$, $R^{10}$, $R^{11}$ and $R^{12}$ are independently selected from the group consisting of hydride, and optionally substituted alkyl, heteroalkyl, aryl, and heteroaryl.

6. A bridged bi-aromatic phenol ligand according to claim 1 wherein the bridging group A is selected from the group consisting of optionally substituted divalent hydrocarbyl and divalent heteroatom containing hydrocarbyl.

7. A bridged bi-aromatic phenol ligand according to claim 1 wherein the bridging group A is selected from the group consisting of optionally substituted divalent alkyl, alkenyl, alkynyl, heteroalkyl, heteroalkenyl, heteroalkynyl, aryl, heteroaryl and silyl.

8. A bridged bi-aromatic phenol ligand according to claim 1 wherein the bridging group A is represented by the general formula —$(QR^{13}{}_{2-z''})_{z'}$— wherein each Q is either carbon or silicon and each $R^{13}$ may be the same or different from the others such that each $R^{13}$ is selected from the group consisting of hydride and optionally substituted hydrocarbyl and heteroatom containing hydrocarbyl, and optionally two or more $R^{13}$ groups may be joined into a ring structure having from 3 to 50 atoms in the ring structure not counting hydrogen atoms; z' is an integer from 1 to 10; and z" is 0, 1 or 2.

9. A bridged bi-aromatic phenol ligand according to claim 1 wherein Ar is, independently, an optionally substituted aryl or heteroaryl.

10. A bridged bi-aromatic phenol ligand according to claim 1 wherein Ar is, independently, an optionally substituted phenyl, naphthyl, biphenyl, anthracenyl or phenanthrenyl.

11. A bridged bi-aromatic phenol ligand according to claim 1 wherein Ar is, independently, an optionally substituted thiophene, pyridine, isoxazole, pyrazole, pyrrole, furan, or benzo-fused analogues of these rings.

12. A bridged bi-aromatic phenol ligand according to claim 1 wherein each occurrence of Ar is the same.

13. A method of preparing a bridged bi-aromatic phenol ligand according to claim 1 comprising the steps of:
   a) treating a bridged bi-aromatic phenol of formula (III) with a source of halogen to yield a tetrahalo bridged bi-aromatic phenol of formula (IV); and

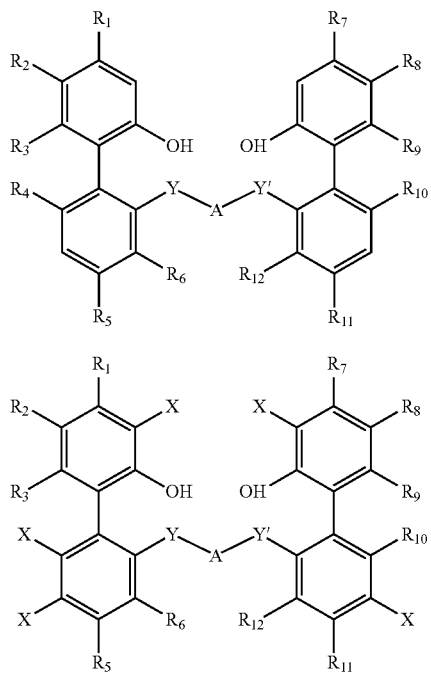

(III)

(IV)

b) treating the tetrahalo bridged bi-aromatic phenol of formula (IV) with an aryl-boron compound (ArBR$^b_2$ or ArBF$_3^-$M$^+$) in the presence of a catalyst, to yield the bridged bi-aromatic phenol ligand of formula (I);

wherein each of R$^1$, R$^2$, R$^3$, R$^4$, R$^5$, R$^6$, R$^7$, R$^8$, R$^9$, R$^{10}$, R$^{11}$ and R$^{12}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is an optionally substituted divalent alkyl, alkenyl, alkynyl, heteroalkyl, heteroalkenyl, heteroalkynyl, carbocycle, heterocarbocycle, aryl, heteroaryl, or silyl; Y and Y' are independently selected from O, S, NR$^a$ and PR$^a$ wherein R$^a$ is optionally substituted hydrocarbyl; Ar is, independently, optionally substituted aryl or optionally substituted heteroaryl; X is halo; R$^b$ is independently selected from hydride, alkyl, hydroxy and alkoxy, wherein when both of R$^b$ are alkoxy, optionally they may combine to form a ring structure of formula BO$_2$R$^b_2$, and wherein M$^+$ is an alkali metal cation.

14. A method according to claim 13 wherein the catalyst comprises palladium or nickel.

15. A method according to claim 14 wherein the palladium catalyst is a palladium phosphine catalyst.

16. A method according to claim 13 wherein the catalyst further comprises a base.

17. A method according to claim 16 wherein the base is an alkali metal carbonate or alkali metal phosphate.

18. A method according to claim 13 wherein X is bromo or chloro.

19. A method according to claim 13 wherein the aryl-boron compound is an optionally substituted aryl boronic acid, an optionally substituted heteroaryl boronic acid, an optionally substituted aryl boronic ester, an optionally substituted heteroaryl boronic ester, an optionally substituted aryl trifluoroborate, an optionally substituted heteroaryl trifluoroborate, an optionally substituted aryl borane or an optionally substituted heteroaryl borane.

20. A transition metal compound comprising a ligand according to claim 1.

* * * * *